US010631885B2

(12) United States Patent
Wilkinson et al.

(10) Patent No.: US 10,631,885 B2
(45) Date of Patent: Apr. 28, 2020

(54) PATIENT-MATCHED TOTAL KNEE ARTHROSCOPY

(71) Applicant: Smith & Nephew, Inc., Memphis, TN (US)

(72) Inventors: Zachary C. Wilkinson, Germantown, TN (US); Nathaniel M. Lenz, Germantown, TN (US); Randy C. Winebarger, Southaven, MS (US)

(73) Assignee: Smith & Nephew, Inc., Memphis, TN (US)

( * ) Notice: Subject to any disclaimer, the term of this patent is extended or adjusted under 35 U.S.C. 154(b) by 1095 days.

(21) Appl. No.: 14/420,434

(22) PCT Filed: Aug. 9, 2013

(86) PCT No.: PCT/US2013/054277
§ 371 (c)(1),
(2) Date: Feb. 9, 2015

(87) PCT Pub. No.: WO2014/026082
PCT Pub. Date: Feb. 13, 2014

(65) Prior Publication Data
US 2015/0196308 A1    Jul. 16, 2015

Related U.S. Application Data

(60) Provisional application No. 61/715,462, filed on Oct. 18, 2012, provisional application No. 61/681,475, filed on Aug. 9, 2012.

(51) Int. Cl.
*A61B 17/15* (2006.01)
*A61B 17/17* (2006.01)

(52) U.S. Cl.
CPC ...... *A61B 17/1764* (2013.01); *A61B 2560/00* (2013.01)

(58) Field of Classification Search
CPC . A61B 17/155; A61B 17/157; A61B 17/1764; A61B 2560/00; A61B 2017/568
(Continued)

(56) References Cited

U.S. PATENT DOCUMENTS 4,841,975 A * 6/1989 Woolson ............. A61B 17/154
378/205
5,417,694 A * 5/1995 Marik .................. A61B 17/155
606/88
(Continued)

FOREIGN PATENT DOCUMENTS

WO    2011106395 A1    9/2011

OTHER PUBLICATIONS

European Patent Office, European Search Report dated Apr. 29, 2016, 8 pages.
(Continued)

*Primary Examiner* — Jessica Weiss
(74) *Attorney, Agent, or Firm* — Pepper Hamilton LLP

(57) ABSTRACT

A gauge assembly includes a distal femur gauge including medial and lateral condyle paddles each having a shape and size corresponding to a pre-operative planned distal resection of a patient's femur, and a tibial cutting block connected to the distal femur gauge. The condyle paddles include features, for example, pin-receiving holes, that permit intra-operative anterior-posterior and/or internal-external adjustment of the position of the distal femur gauge. The tibial cutting block includes features, for example, pin-receiving slot and holes, that permit fixing of the varus-valgus and flexion-extension degrees of freedom prior to fixing the internal-external and medial-lateral degrees of freedom.

11 Claims, 30 Drawing Sheets

(58) Field of Classification Search
USPC .................... 606/86 R–89, 96–98, 79–80
See application file for complete search history.

(56) References Cited

U.S. PATENT DOCUMENTS

| | | | | | |
|---|---|---|---|---|---|
| 6,632,225 | B2* | 10/2003 | Sanford | ............... | A61B 17/154 606/87 |
| 7,371,240 | B2* | 5/2008 | Pinczewski | .......... | A61B 17/154 128/898 |
| 8,313,491 | B2* | 11/2012 | Green, II | ............. | A61B 17/155 606/87 |
| 8,323,288 | B2* | 12/2012 | Zajac | ................... | A61B 17/155 606/88 |
| 9,393,028 | B2* | 7/2016 | Schuster | .............. | A61B 17/155 606/87 |
| 10,028,750 | B2* | 7/2018 | Rose | ................... | A61B 17/155 606/96 |
| 2004/0220583 | A1* | 11/2004 | Pieczynski, II | .... | A61B 17/1764 606/102 |
| 2006/0004374 | A1* | 1/2006 | Griner | .................. | A61B 17/155 606/88 |
| 2006/0142778 | A1* | 6/2006 | Dees, Jr. | ............ | A61B 17/1764 606/88 |
| 2006/0217734 | A1* | 9/2006 | Sanford | ............... | A61B 17/155 606/88 |
| 2007/0173854 | A1* | 7/2007 | Berger | ................. | A61B 17/157 606/88 |
| 2009/0087276 | A1* | 4/2009 | Rose | .................... | A61B 17/155 409/79 |
| 2009/0088759 | A1* | 4/2009 | Aram | ................... | A61B 17/155 606/87 |
| 2009/0099567 | A1* | 4/2009 | Zajac | ................... | A61B 17/155 606/79 |
| 2010/0305575 | A1* | 12/2010 | Wilkinson | ........... | A61B 17/155 606/88 |
| 2011/0071533 | A1* | 3/2011 | Metzger | ............... | A61B 17/157 606/88 |
| 2011/0218545 | A1* | 9/2011 | Catanzarite | .......... | A61B 17/155 606/96 |
| 2012/0041446 | A1* | 2/2012 | Wong | ................. | A61B 17/1703 606/96 |
| 2012/0277751 | A1* | 11/2012 | Catanzarite | .......... | A61B 17/155 606/88 |

OTHER PUBLICATIONS

European Patent Office, First Office Action dated Oct. 18, 2017, 4 pages.
International Search Report and Written Opinion for PCT/US2013/054277 dated Nov. 14, 2013.

* cited by examiner

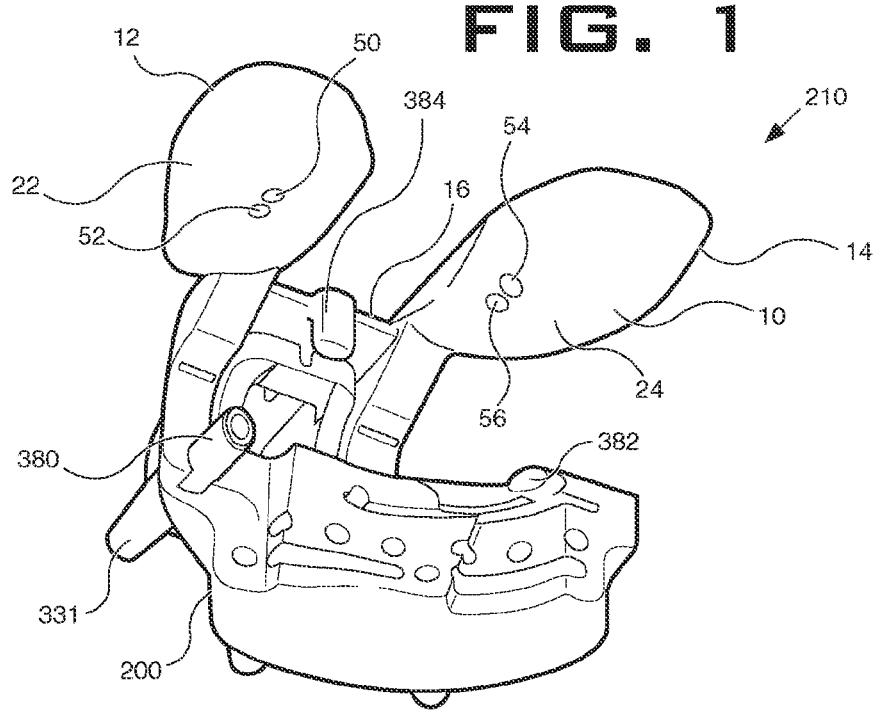
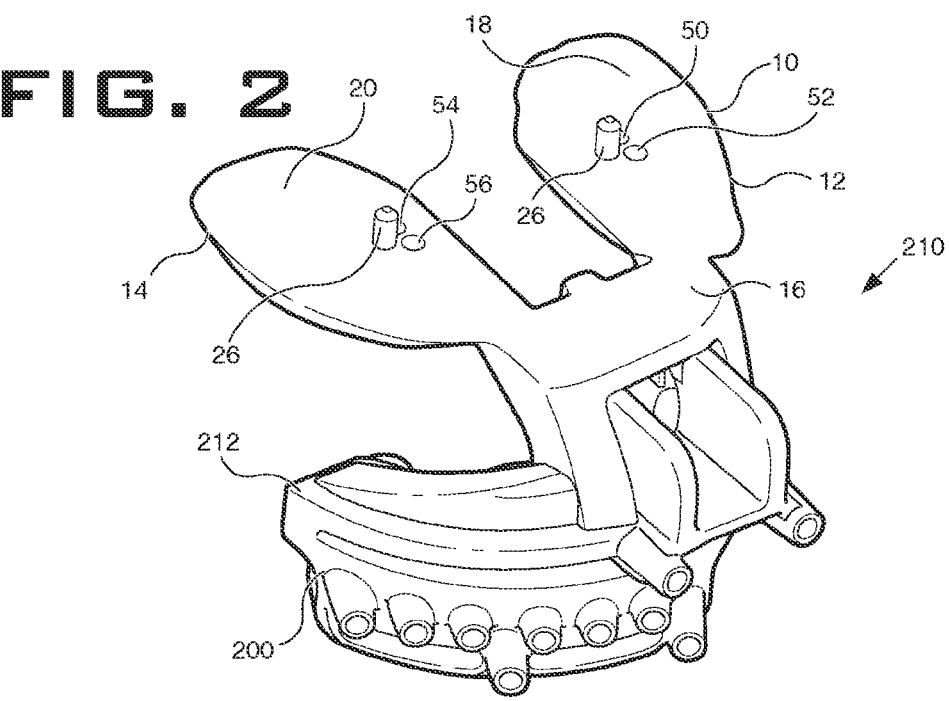

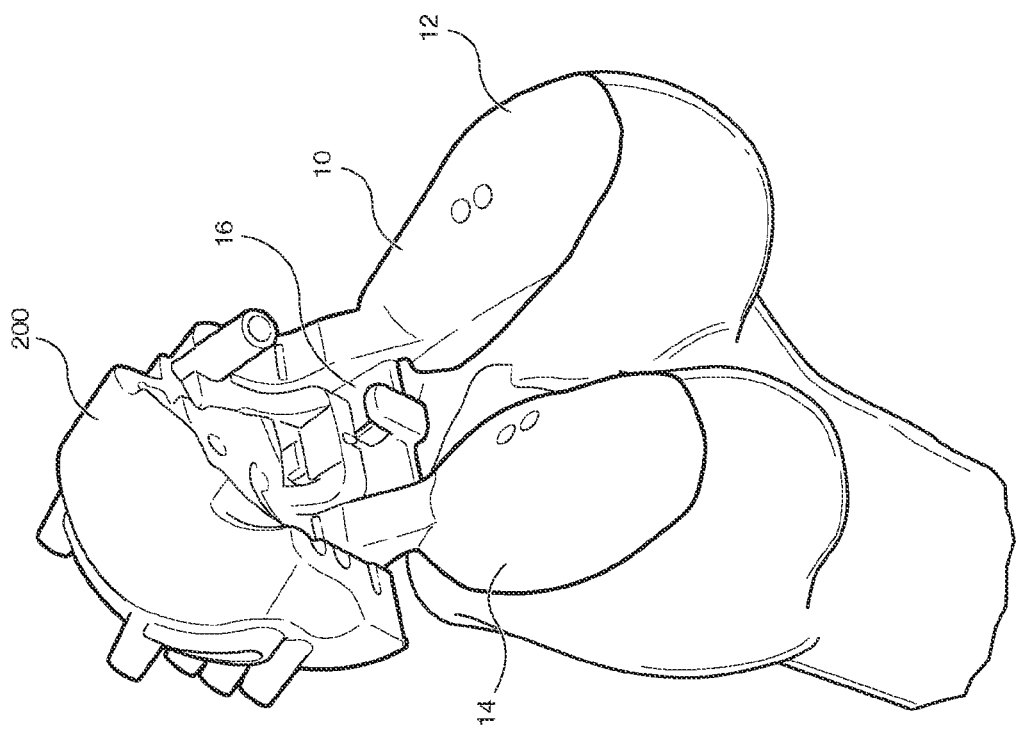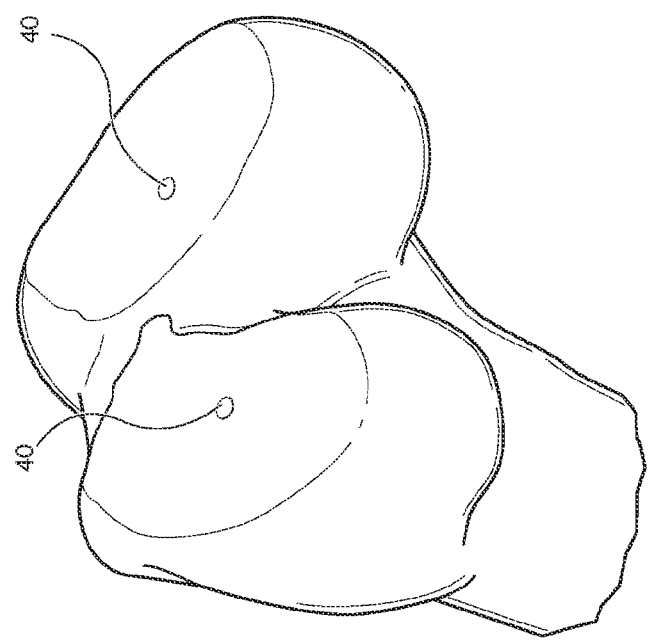

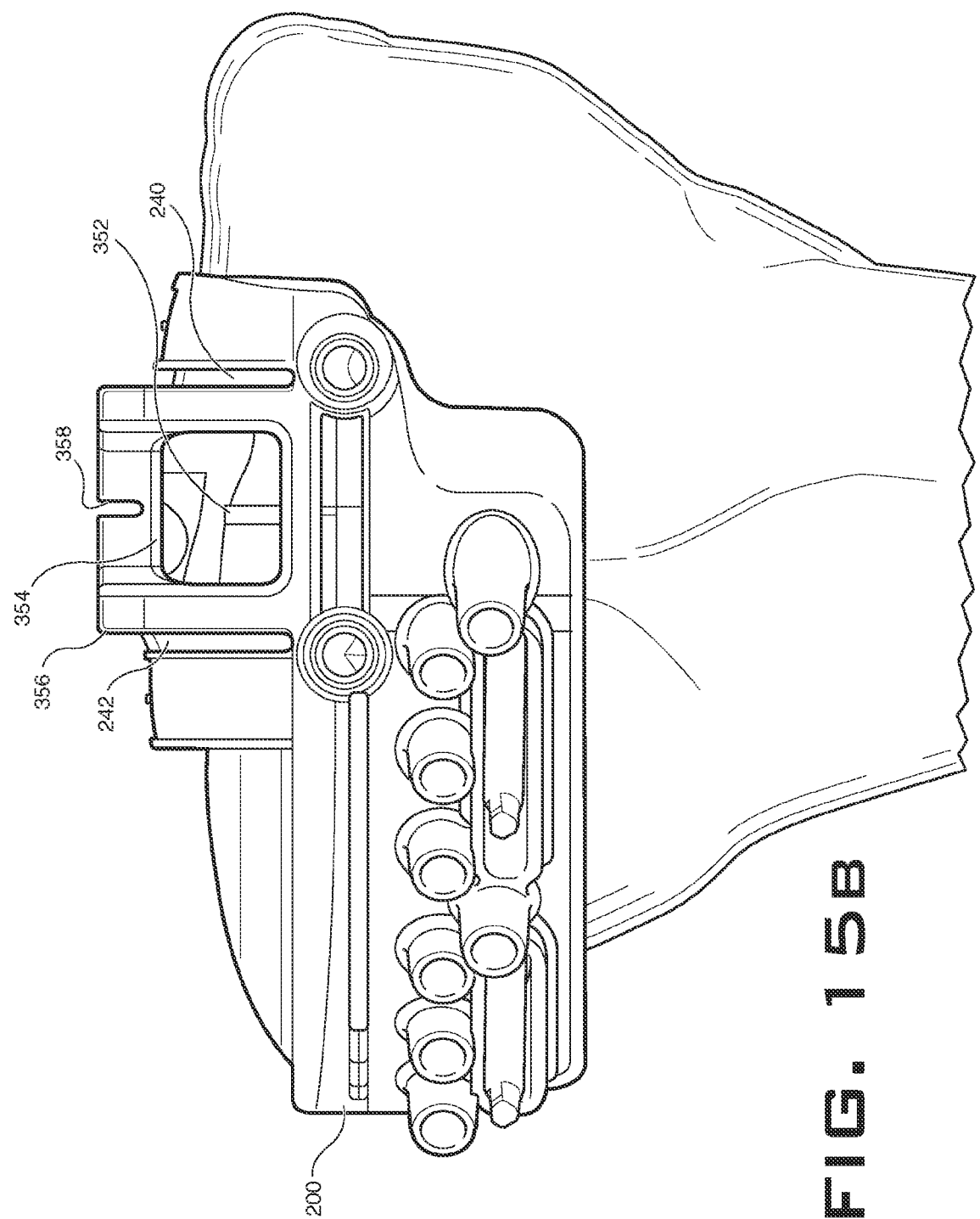

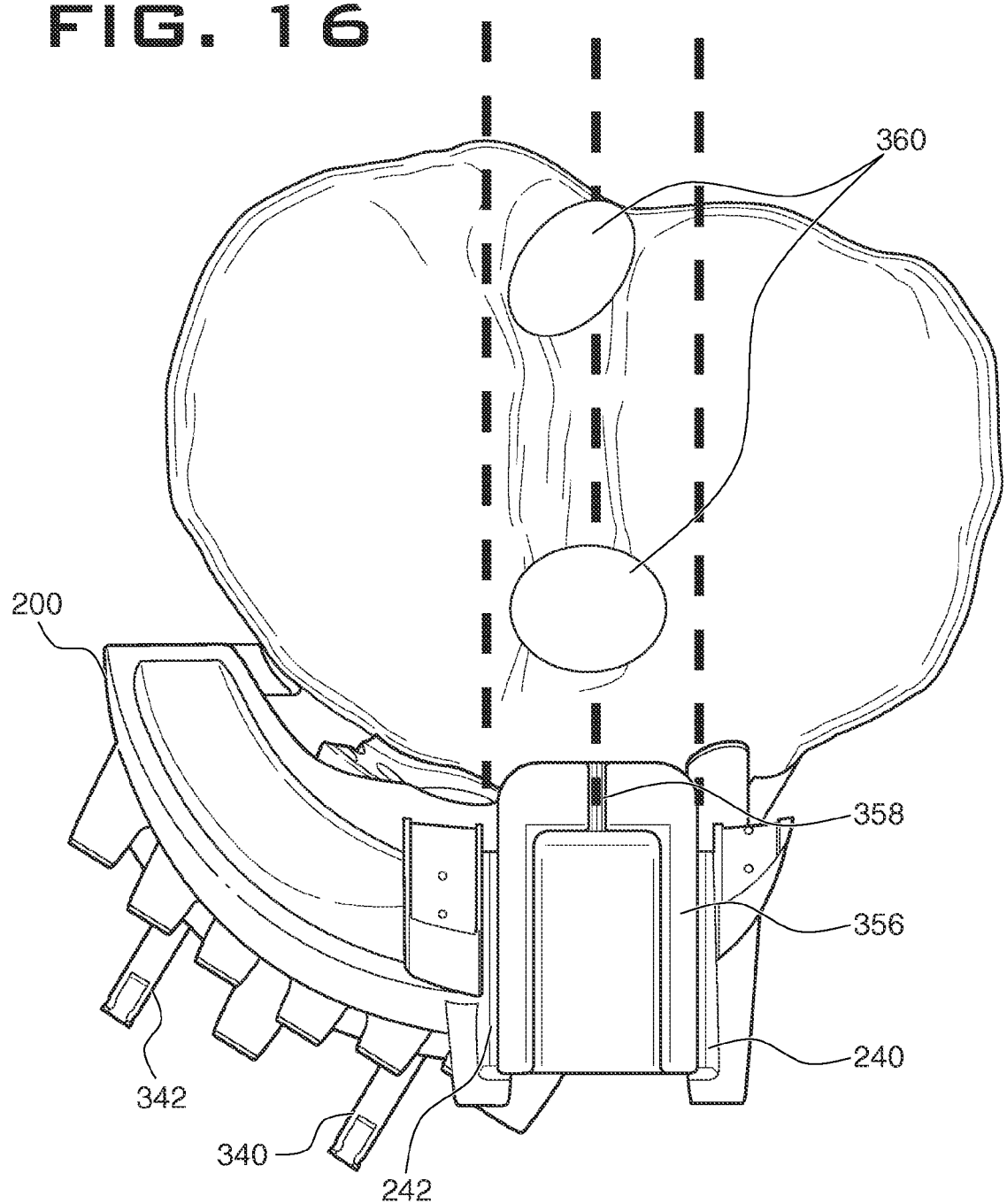

PRIOR ART

Prior Art

PATIENT-MATCHED TOTAL KNEE ARTHROSCOPY

CROSS-REFERENCE TO RELATED APPLICATIONS

This application is a United States National Phase filing of International Application No. PCT/US2013/054277, filed Aug. 9, 2013, which claims priority to and the full benefit of U.S. Provisional Application Ser. No. 61/681,475, filed Aug. 9, 2012, and titled "PATIENT-MATCHED TOTAL KNEE ARTHROPLASTY", and U.S. Provisional Application Ser. No. 61/715,462, filed Oct. 18, 2012, and titled "PATIENT-MATCHED TOTAL KNEE ARTHROPLASTY," the entire contents of each prior application are incorporated herein by reference.

BACKGROUND

Patient-matched cutting guides are used during orthopaedic procedures to guide resections to bone. The patient-matched guides are generally based on data received from an MRI or CT scan of the patient and rely on matching an anatomic feature for correct positioning of the guide during a surgical procedure. In some total knee arthroplasty procedures, a patient-matched cutting guide is used to form a distal femur resection. As illustrated in FIGS. 21 and 22, the cutting guide 600 includes a resection slot 602 that receives and guides a saw blade for forming the distal femur resection. The resection slot 602 is positioned and orientated in the guide 600 based on a pre-operative plan. The cutting guide 600 includes pin holes 604, 606 that set the rotation and translation of subsequent resections to the femur.

SUMMARY

A gauge assembly enables an operator to verifying that that the intra-operative distal femur resection matches the pre-operative plan, and to make intra-operative adjustments to the pre-operative plan.

According to one aspect, a distal femur gauge includes a medial condyle paddle and a lateral condyle paddle connected to the medial condyle paddle. Each condyle paddle has a shape and size corresponding to a pre-operative planned distal resection of a patient's femur.

Embodiments of this aspect may include one or more of the following features.

The condyle paddles are replicas of pre-operative planned condyle resections. Alternatively, the condyle paddles are shaped and sized to correct for limb mal-alignment. The condyle paddles include features, for example, pin-receiving holes, that permit intra-operative anterior-posterior and/or internal-external adjustment of the position of the distal femur gauge.

According to another aspect, a gauge assembly includes a distal femur gauge including medial and lateral condyle paddles each having a shape and size corresponding to a pre-operative planned distal resection of a patient's femur, and a tibial cutting block connected to the distal femur gauge.

Embodiments of this aspect may include the tibial cutting block defining a plateau resection slot.

According to another aspect, a gauge assembly includes a distal femur gauge including medial and lateral condyle paddles, and a tibial cutting block connected to the distal femur gauge. The tibial cutting block includes features, for example, pin-receiving slots and holes that permit fixing of the superior-inferior, varus-valgus and flexion-extension degrees of freedom prior to fixing the internal-external and medial-lateral degrees of freedom. The features may also permit alteration of previously fixed degrees of freedom should they prove in need of correction.

According to another aspect, a method of intra-operatively adjusting a pre-operative plan includes intra-operatively adjusting the anterior-posterior and/or internal-external position of a distal femur gauge. The distal femur gauge includes medial and lateral condyle paddles each having a shape and size corresponding to a pre-operative planned distal resection of a patient's femur. The method further includes intra-operatively adjusting the internal-external and medial-lateral degrees of freedom of a patient-matched tibial cutting block after fixing of the varus-valgus, flexion-extension and superior-inferior degrees of freedom of the cutting block. The method may also include the resetting of previously fixed degrees of freedom after resections have been made.

According to another aspect, a method of intra-operatively assessing a pre-operative planned distal femur resection includes placing a distal femur gauge on the resected femur and placing the patient's leg in extension to assess alignment of the patient's femur and tibia. The distal femur gauge includes medial and lateral condyle paddles each having a shape and size corresponding to a pre-operative planned distal resection of a patient's femur.

According to another aspect, a gauge assembly includes a distal femur gauge including medial and lateral condyle paddles and a tibial cutting block connected to the distal femur gauge. The tibial cutting block defines a proximal tibial resection plane. The gauge assembly includes a flexible element that permits adjustment of the posterior slope of the proximal tibial resection plane.

BRIEF DESCRIPTION OF THE DRAWINGS

FIG. 1 is a perspective view of a gauge assembly including a distal femur gauge and a tibial cutting block.

FIG. 2 is another perspective view of the gauge assembly of FIG. 1.

FIG. 3 illustrates a distal resection of a femur.

FIG. 4 illustrates the gauge assembly of FIG. 1 placed on the distal resection of the femur.

FIGS. 15A and 15B illustrate the gauge assembly of FIG. 13 repositioned on the pins.

FIG. 16 is a top view of the patient's tibia showing the cruciate ligaments.

DETAILED DESCRIPTION

Figure 6:
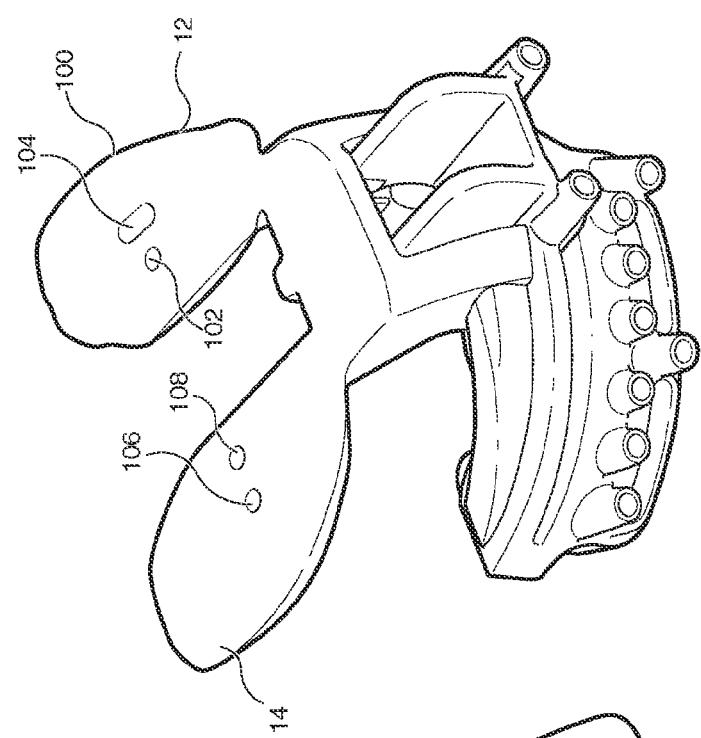
FIGS. 5 and 6 are perspective views of another embodiment of a gauge assembly.

Problems that may be encountered during total knee arthroplasty include the inability to I) verify whether the intra-operative distal femur resection matches the pre-operative plan; II) validate the functionality of the intra-operative distal cut; III) intra-operatively adjust pre-operative decisions based on the assessment of the intra-operative results; and IV) avoid the interactions between and error propagations amongst the several degrees of freedom due the design of conventional PM instrumentation.

I. Verify Intra-Operative Distal Cut to Pre-Operative Plan

Without an intramedullary rod or computer assisted surgery, the distal femur resection is difficult to orient and to verify. A patient-matched guide uses the anatomy of the femur as an intermediate datum by which to orient the distal femur resection; however, errors in the resection can be made due to a host of sources—poor fit, poor placement, movement during pinning, lack of saw blade constraint, skiving of the saw blade, etc. Verifying that that the intra-operative distal femur resection matches the pre-operative plan is important because all subsequent resections, decisions and outcomes are in some way impacted by the distal femur resection. Also, when a patient-matched femur implant is used, disagreement between the intra-operative and pre-operative planned distal resections can have an impact on the resulting profile match of the patient specific femoral implant and the profiles of the anterior, posterior, and anterior/posterior chamfer resection profiles. Also, should the patient specific femoral implant seek to cause a patient-specific kinematic pattern, small shifts of the intra-operative distal femur resection from the pre-operative plan can negatively alter the resulting kinematics/kinetics of the patient specific implant(s).

Referring to FIGS. 1 and 2, to verify whether an intra-operative distal resection matches the pre-operative plan, a distal femur gauge 10 can be used to compare the shape of the pre-operative-planned distal femur resection profile to the intra-operative distal femur resection profile. If the resection is not correct per the pre-operative plan, mismatch between the distal femur gauge 10 and the distal femur resection profile is seen. Based on any mismatch, the operator can assess whether and what kind of a recut is necessary or, alternatively, if the profiles match, the operator gains confidence in the initial resection and continues with the surgery.

The distal femur gauge 10 includes medial and lateral condyle paddles 12, 14 connected by a bridge 16. The distal femur gauge 10 can be attached to a patient-matched tibial cutting block 200, discussed below, to form a guide assembly 210. Each of the paddles includes a proximal-facing surface 18, 20, respectively, and distal-facing surface 22, 24, respectively. Extending from each of the proximal-facing surfaces 18, 20 is a protruding pin 26. The proximal-facing surfaces 18, 20 are flat surfaces designed to conform to the distal femur after making the distal resection of the femur. In a patient-matched system, the condyle paddles 12, 14 can be replicas of the patient's condyles that are intended to be cut away from the distal femur. The distal-facing surfaces 22, 24 are contoured to match the contour of the native condyles, the thickness profile of the condyle paddles match that of the native condyles, and the sagittal and coronal curves match those of the native condyles. Alternatively, the condyle paddles can correspond to a specific implant size matching one or more particular dimensions of the idealized patient anatomy. In either case, as discussed below, the condyle paddles can be designed to address a native bone mal-alignment.

Referring to FIGS. 3 and 4, in use, after performing a distal resection of the distal femur using, for example, a patient-matched cutting guide, the distal femur gauge 10 is positioned over the resection with pins 26 received in holes 40 previously formed during the distal resection. FIG. 4 shows a match between the profiles of the condyle paddles 12, 14 and the resected femur, which provides the surgeon with confidence that the distal resection was made according to the pre-operative plan.

II. Validate Functionality of Intra-Operative Distal Cut

Typically with patient-matched or standard total knee arthroplasty, "measured" distal femur and proximal tibia resections are made. Then, these two resections are gauged against one another (with a gauge representing the femur plus tibia implants' thicknesses) to ensure that an adequate sum of bone is removed for the implants. But this method does not ensure that the correct location of bone has been removed. For instance, upon finding an inadequacy (i.e. the sum of bone removed is insufficient relative to a femur plus tibia implant gauge), one cannot determine whether additional bone should be resected from the tibia or the femur. This uncertainty is due to the loss of information related to the location of the native joint line. This information is present as long as either the native proximal tibia or distal femur (or both) are intact, but when both are resected, the original information is lost. Therefore, it is desirable to gauge the adequacy of a single resection, whether the distal femur resection or the proximal tibia resection, before making the resection to the second bone.

The distal femur gauge 10 can be used to compare the extension space created by the pre-operative-planned distal femur resection to the extension space created by the intra-operative distal femur resection. In this way, one can verify that the resection was made appropriately and has the desired effect of enabling the limb to return to full extension. The distal femur gauge 10 effectively evaluates the level of the distal femur resection against the native joint line represented by the native tibial articular geometry.

In use, the operator puts the leg in extension placing the distal-facing surfaces 22, 24 of the distal femur gauge 10 against the native tibia. If the limb cannot return to full extension (i.e. flexion contracture), then this indicates that too little distal femur has been resected. By how much the distal femur has been under resected can be gauged by simulating a distal femur recut through removing thickness from the distal femur gauge in increments of 1 mm, as described in US Published Application No. 2010/0305575, titled Method and Apparatus for Performing Knee Arthroplasty, hereby incorporated by reference in its entirety. It has been found that 1 mm of Distal Femur Gauge thickness reduction will allow between 1 and 2 degrees of additional extension. If instead of flexion contracture, the limb exhibits hyperextension, this indicates that too much distal femur has been resected. Material can then be added to the distal femur gauge 10 in 1 mm increments resulting in 1-2 degrees of reduced extension. In this way one can gauge exactly how much the distal femur has been under or over resected relative to the native joint line as represented by the native tibial articular geometry. This information is useful as it can directly or indirectly affect subsequent decisions and outcomes.

If the operator determines that the distal femur resection matches the pre-operative plan, the patient-matched tibial cutting block 200 can be used to form the tibial resection, as discussed below. A drop down rod (not shown) can be coupled to the cutting block 200 to assess alignment of the tibia and femur, i.e., the alignment of the entire limb, in multiple planes prior to pinning the block 200 in place and forming the tibial resection.

III. Intra-Operatively Adjust Pre-Operative Plan Based on Assessment of Intra-Operative Results As discussed above, one can gauge how much the distal femur has been under or over resected relative to the native joint line as represented by the native tibial articular geometry. This information can affect subsequent decisions and outcomes to arrive at the desired alignment and flexion/extension balance. To enable the operator to respond to this information, the operator preferably has the ability to adjust intra-operatively the posterior femur resection before the posterior femur resection is made, and the proximal tibial resection before and after the resection is made. The more native structures which are retained, the greater the importance of having the ability to make these adjustments to achieve alignment and balance.

a. Ability to Adjust Posterior Femur Resection Before the Resection is Made

Referring again to FIGS. 1-3, the holes 40 are intended to act as an intermediary datum for guidance of the saw guide for the remaining femur resections. If the operator determines intra-operatively that the anterior-posterior position and/or internal-external rotation of the additional femoral resections should be adjusted from that of the pre-operative plan (for example, as discussed in US Published Application No. 2010/0305575, ultra), alternative pin holes 50, 52, 54, and 56 defined by the paddles 12, 14 can be used to alter the location of the holes 40. The operator can choose holes 50 and 54 or holes 52 and 56 to adjust the anterior-posterior position, or holes 50 and 56 or holes 52 and 54 to adjust the internal-external rotation. The operator drills through the chosen set of holes to form new holes 40 that are used to position a saw guide for making the remaining femur resections. Use of a discreet set of pin holes is best used for known/controlled changes in anterior-posterior position. Changing the position of holes 40 can improve alignment of the femur implant to the femur, and/or create a more desirable flexion/extension balance.

Figure 5:
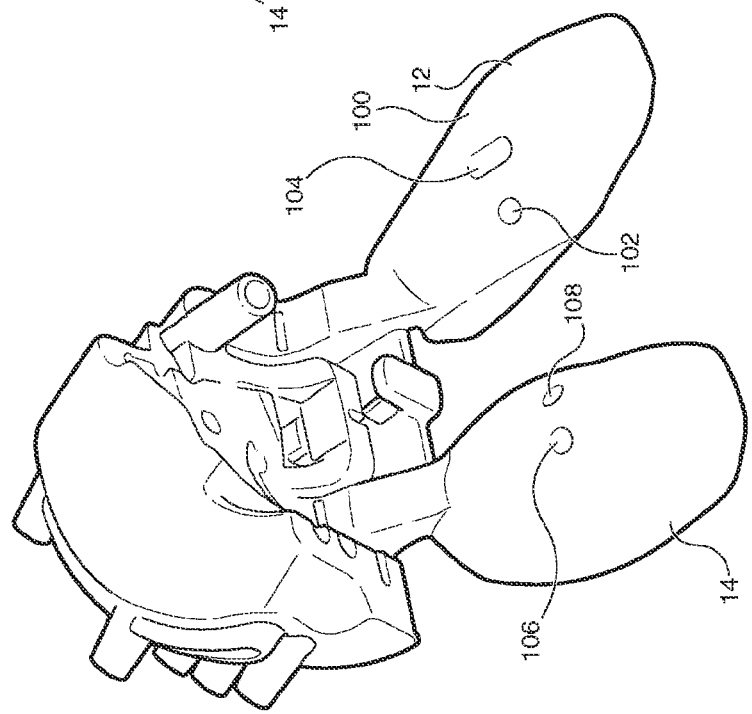

Referring to FIGS. 5 and 6, if an operator wants more freedom to fine tune the internal-external degree of freedom, the distal femur gauge 10 can be removed and an alternative gauge 100 can be positioned on the distal femur. The gauge 100 corresponds to gauge 10 except that instead of pin 26 and holes 50, 52, 54, and 56, the paddle 12 defines a hole 102 and a slot 104, and the paddle 14 defines two holes 106, 108.

Figure 8:
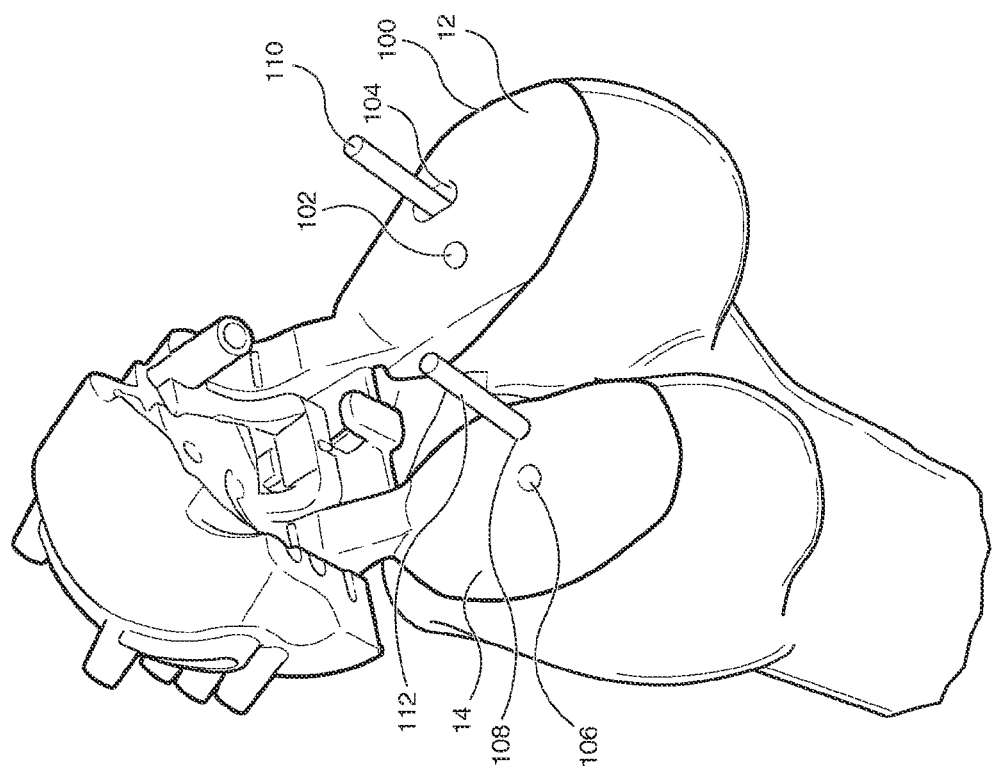
FIG. 8 illustrates the gauge assembly of FIG. 5 placed on the distal resection of the femur.
Figure 7:
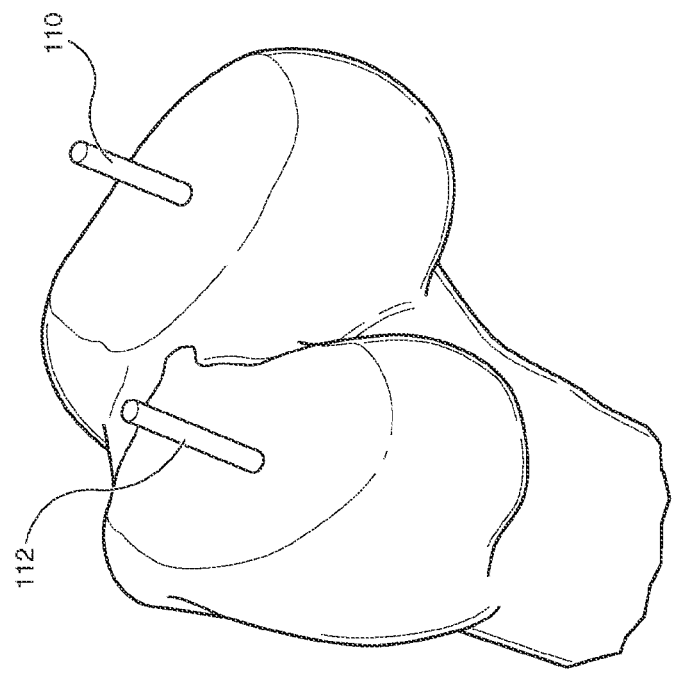
FIG. 7 illustrates a distal resection of a femur with pins extending from the femur.

Referring to FIGS. 7 and 8, in use of gauge 100, pins 110, 112 are guided by the patient-matched distal femur resection guide into the distal femur and remain in place after the distal femur resection. The operator places the gauge 100 over the distal femur with pin 110 passing through slot 104 and pin 112 passing through hole 108. The operator moves the gauge 100 on the surface of the resected distal femur fine tuning the internal-external rotation and/or the anterior-posterior translation. Gauge 100 could also be used to fine tune the anterior-posterior degree of freedom by including a slot in paddle 14 as well. When the gauge 100 is optimally positioned, holes 102, 106 are used to form holes in the distal femur that act as the intermediary datum by which the saw guide for the remaining femur resections is positioned.

b. Ability to Adjust the Proximal Tibial Resection Before and After the Resection is Made When the gauge 10 is placed onto the distal femur resection and allowed to articulate with the native tibia in full passive extension, the limb will return to its pre-distal-resection alignment if the articular shapes of the gauge 10 are not altered to correct for any deformity. If the pre-distal-resection alignment of the limb is determined to be inadequate (i.e. varus or valgus deformity worth correcting), the gauge 10 can be designed pre-operatively to deviate from the resected native distal femur bone to correct for the pre-operatively detected deformity. Such deviations can be induced in order to alter/correct the mechanical axis mal-alignment between the diseased femur and tibia. The gauge 10 allows for pre-operative and intra-operative adjustment of the offset of a particular distal femur condyle (medial or lateral) as one way to adjust varus/valgus alignment of the limb. This offset could be accomplished pre-operatively and manufactured as a single piece design or a kit of single piece designs or as a kit of modular pieces with each single piece or alternative assembly representing some alteration to one or more degrees of freedom: tibial resection amount or varus/valgus.

If in full extension the operator finds that the coronal alignment is acceptable but the sagittal alignment requires adjustment, the operator can select from one of two or more sets of parallel pin guides representing a tibial slope angle which best aligns to the tibia sagittally, as describe below. Also, should the operator find that after making the tibial resection that the flexion space is unacceptably tight, the operator can choose to increase the slope of the tibial resection. The operator can do so using alternative pin guides.

If in seeking to correct varus/valgus mal-alignment between the tibia and femur one is limited by the soft tissues, this can be an early contraindication for certain types of knee prosthesis or it can be an early indication that soft tissue manipulation is needed before continuing with a particular knee prosthesis.

When the operator finds the extension coronal and sagittal alignment acceptable, the operator will then place two parallel pins through the selected set of tibia pin guides. Thus, after using these pins as intermediary datums to make the tibial resection, the operator can expect the limb to return to the pre-tibial resection coronal and sagittal alignment with the femur and tibial trials and implants in place.

In total knee arthroplasty procedures where it is critical that the tibial internal-external rotation and medial-lateral translation degrees of freedom be fixed prior to the tibial resection (i.e. in a bicruciate retaining tibial procedure) it is beneficial to defer the setting of these degrees of freedom until after the varus-valgus and flexion-extension degrees of freedom are fixed.

Figure 9:
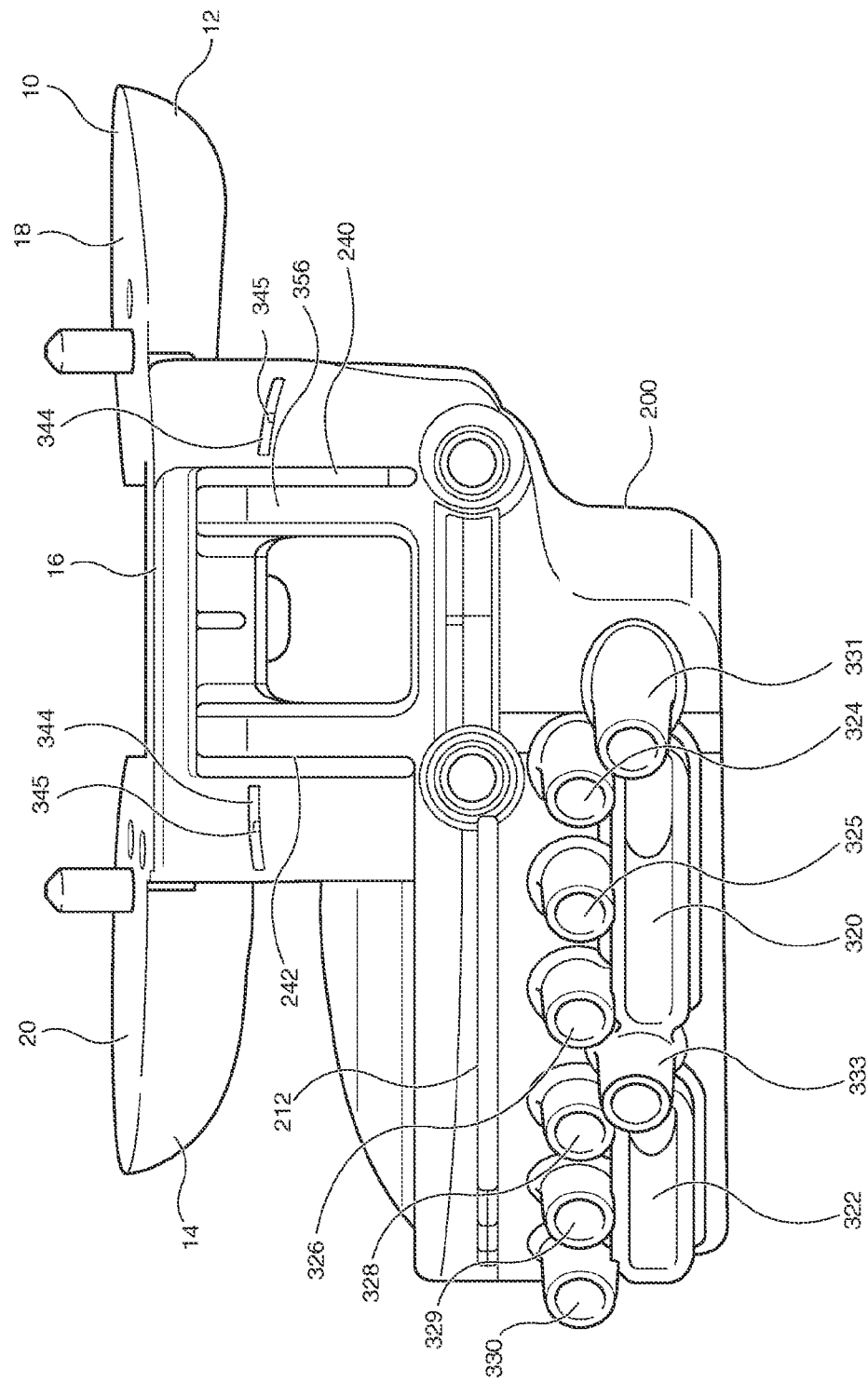
FIG. 9 is another view of the gauge assembly of FIG. 1.

Referring to FIG. 9, to allow fixing of the varus-valgus and flexion-extension degrees of freedom prior to fixing the internal-external and medial-lateral degrees of freedom, the tibial cutting block 200 includes slots 320, 322, which are configured parallel with the tibial resection plane, i.e., resection slot 212. In use, the slots 320, 322 receive two parallel pins protruding from the anterior tibia. The slots 320, 322 enable medial-lateral and internal-external movement of the block on the pins and thus in the plane of the pins. The cutting block 200 also includes pin guide holes 324, 325, 326, 328, 329, 330. With pins placed through the pin guide holes, the varus-valgus, flexion-extension, and depth of the tibial resection are set.

The cutting block 200 includes a set of patient-matched features 380, 382 (FIG. 1), which reference native tibial anatomy and provide that for a given medial-lateral position, the internal-external rotation is appropriate for best fit and coverage of the implant and bone. The patient-matched features 380, 382 help to constrain internal-external rotation of the cutting block 200 as the cutting block is maneuvered. An alignment member 356 of the cutting block 200 can be referenced with the femur or femoral trial such that tibial eminence defining cutting slots 240, 242 of the gauge 10 can be positioned so as to be compatible with the orientation of the femur implant in flexion and or extension. The cutting block 200 includes an alignment member 356 has a width equal to that of the vertical resections which define the boundaries of the preserved eminence. This width enables visualization of where the planned eminence defining resections will be made relative to native cruciate ligament footprints. The bridge 16 includes a protuberance 384 (FIG. 1), which serves as a hyperextension stop that can be removed if desired.

The proximal tibial resection plane, i.e., the location of the plateau resection slot 212 is shifted downward from the distal femur resection contacting surfaces 18, 20 of the gauge 10 by an amount equal to the distance between the pin guide holes 324, 325, 326, 328, 329, 330 and the pin slots 320, 322, for reasons discussed below. The pin guide holes are used in sets 324, 328; 325, 329; and 326, 330 that vary by 2 degrees of posterior slope relative to the tibial mechanical axis. Additional recut pin guides 331, 333 can provide additional slope and/or depth adjustability. Patient-matched feature 380 is located on pin guide 331.

In use, the operator verifies acceptable full limb passive extension with a drop rod (not shown) running the full length of the limb and connected to a particular pin set (324, 328; 325, 239; or 326, 330). If the operator determines that the alignment of the entire limb is acceptable but that the sagittal alignment of the tibial cutting slot 212 relative to the tibial axis is unacceptable, the operator can alter the sagittal alignment in isolation and verify that it is acceptable by moving the drop rod connector from one pin guide set to the alternatively sloped pin set.

Figure 10:
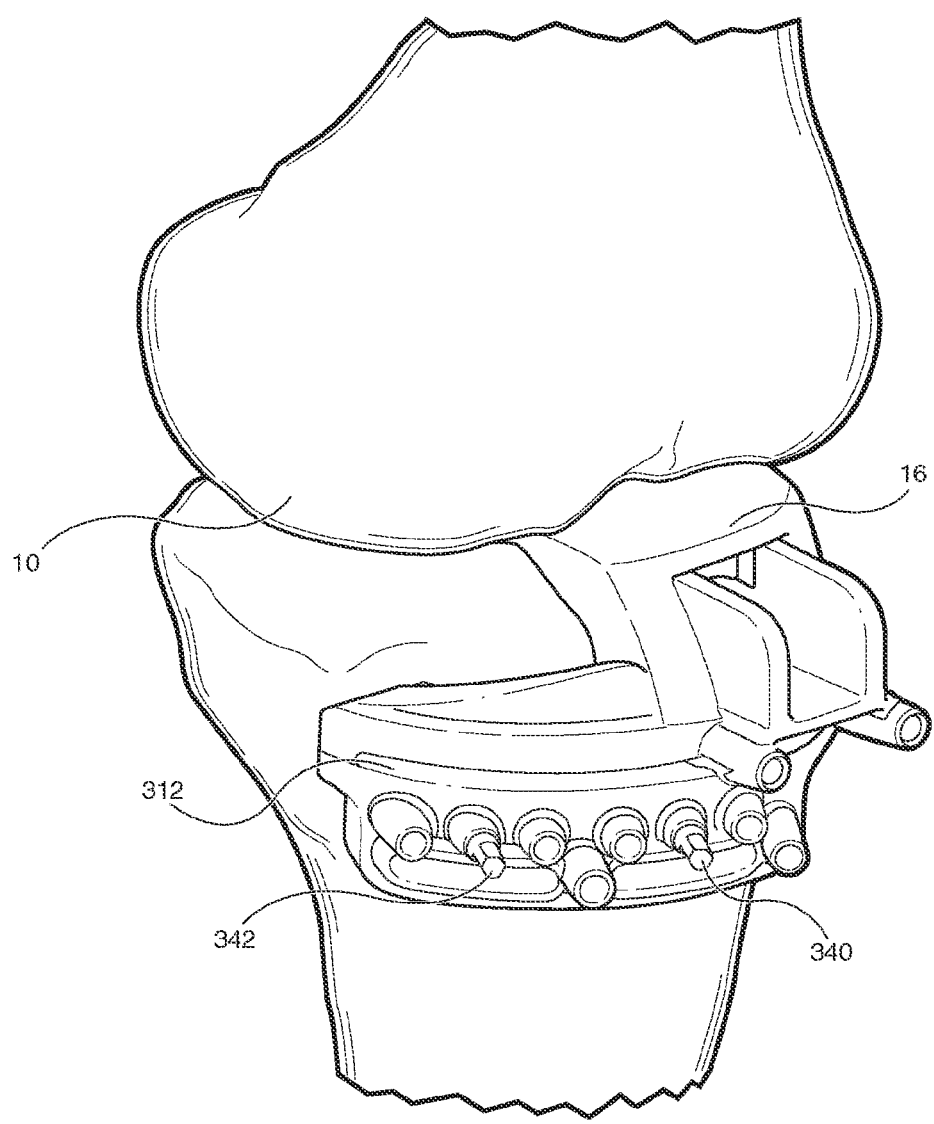
FIG. 10 illustrates the gauge assembly of FIG. 1 positioned between the femur and tibia.
Figure 11:
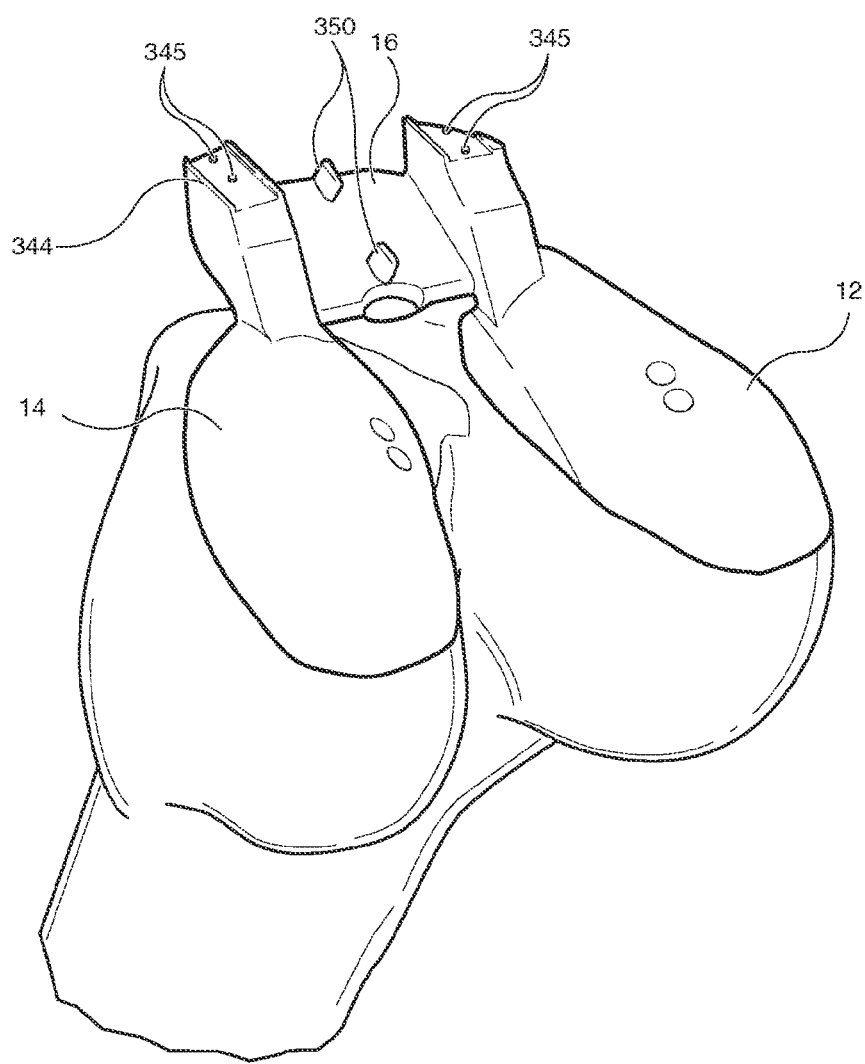
FIG. 11 is a view of the distal femur gauge on the femur after the distal femur gauge and tibial cutting block have been separated.
Figure 13A:
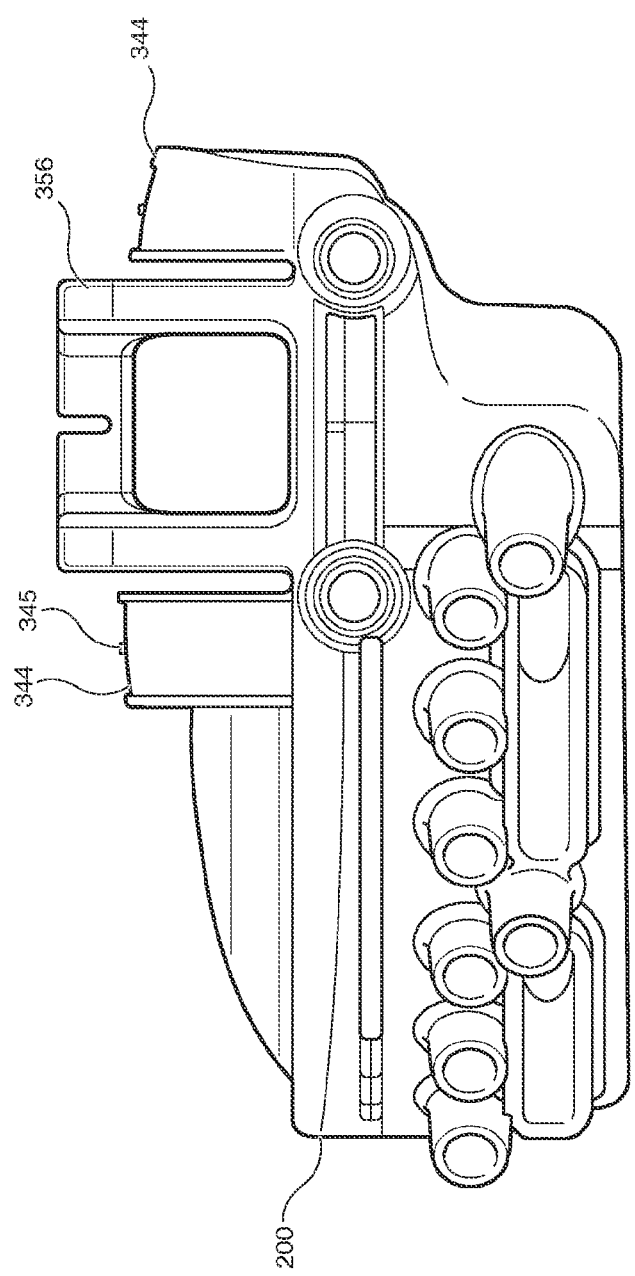
FIGS. 13A and 13B are views of the tibial cutting block after being separated from the distal femur gauge.
Figure 13B:
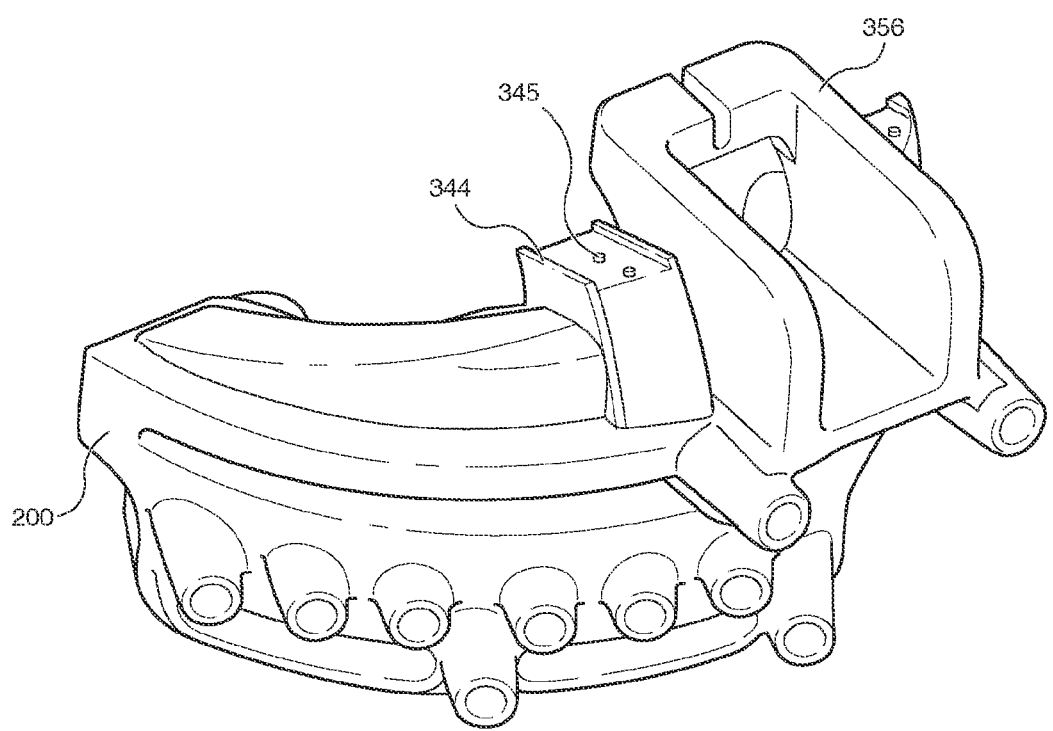

Referring to FIG. 10, with alignment acceptably achieved, the operator drills and/or pins through the desired pin guide set on the tibia, i.e., the set the drop rod was connected to when alignment was established, and places pins 340, 342 through the pin guide holes into the tibia, fixing the varus-valgus and flexion-extension degrees of freedom. The operator then cuts the paddles 12, 14 of the gauge 10 from the patient-matched tibial cutting block 200 (FIGS. 11, 13A and 13B). The paddles 12, 14 can be attached to the cutting block 200 by a pair of cuttable or frangible webs 344) reinforced with columns 345 or other features which are conducive to 1) resistance to unintentional movement or separation between the two connected components and 2) quick intentional separation of the two components.

Figure 12:
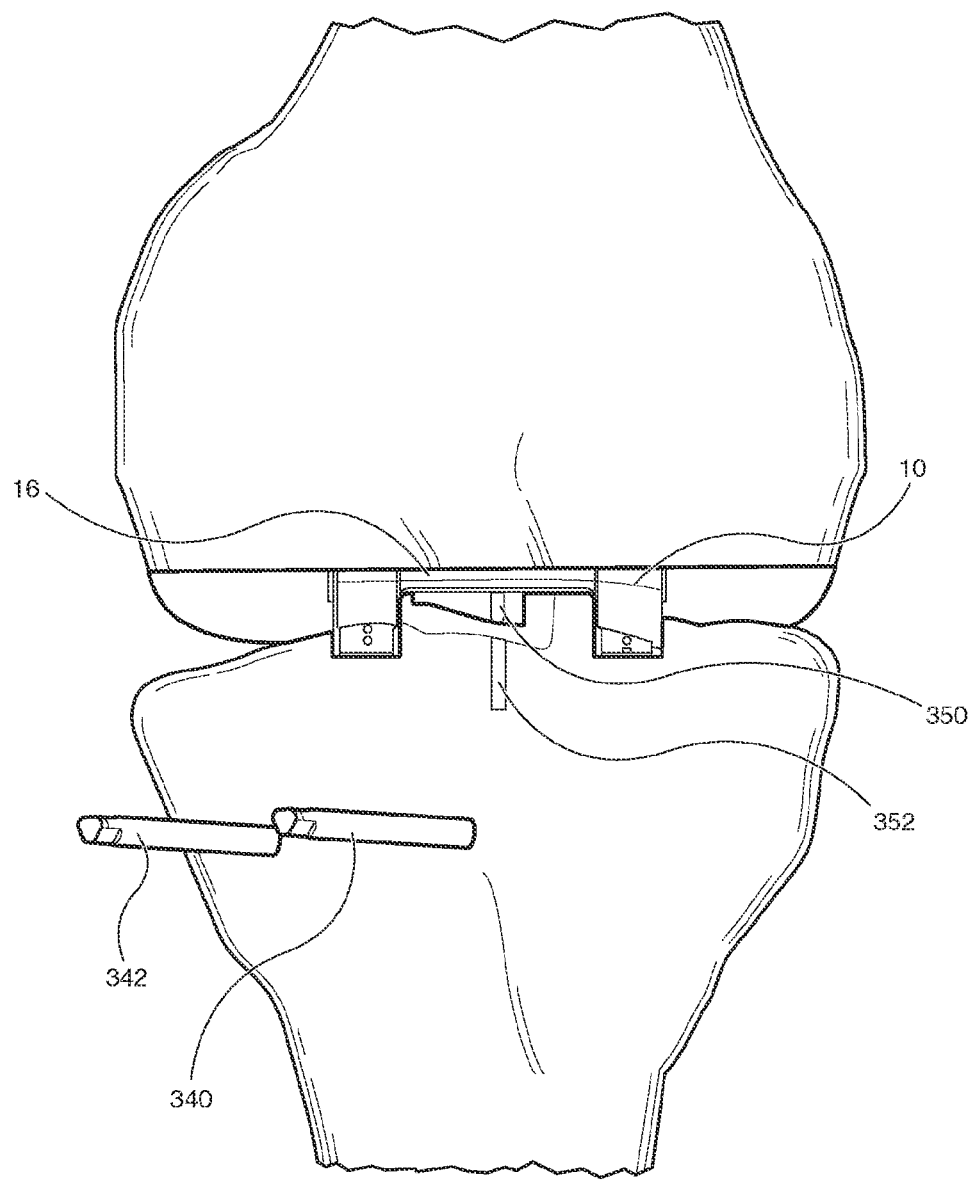
FIG. 12 shows the patient's leg in extension with the distal femur gauge of FIG. 11 positioned between the femur and tibia.
Figure 14:
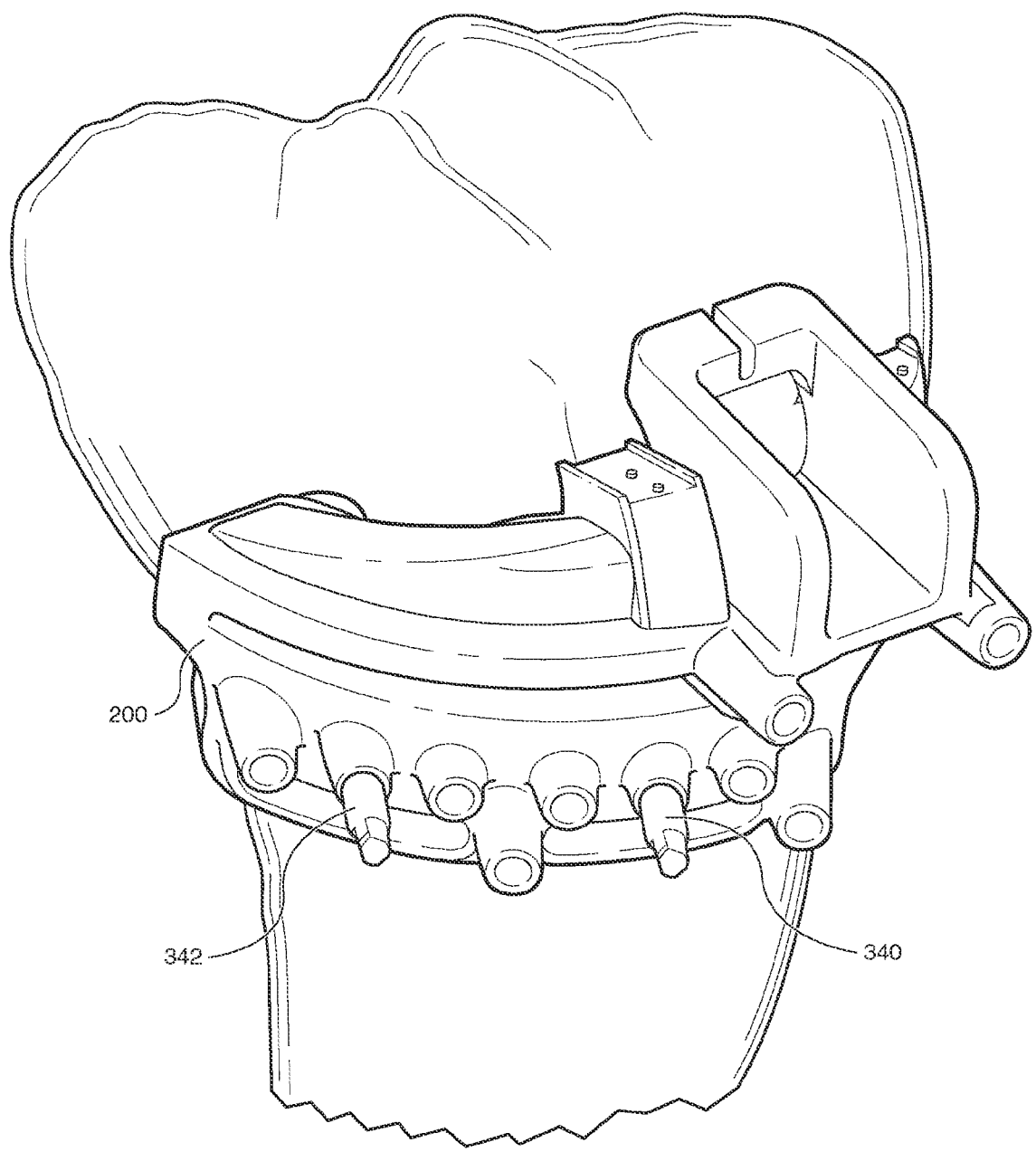
FIG. 14 illustrates the gauge assembly of FIG. 13A pinned to the tibia with the patient's leg in flexion.
Figure 15A:
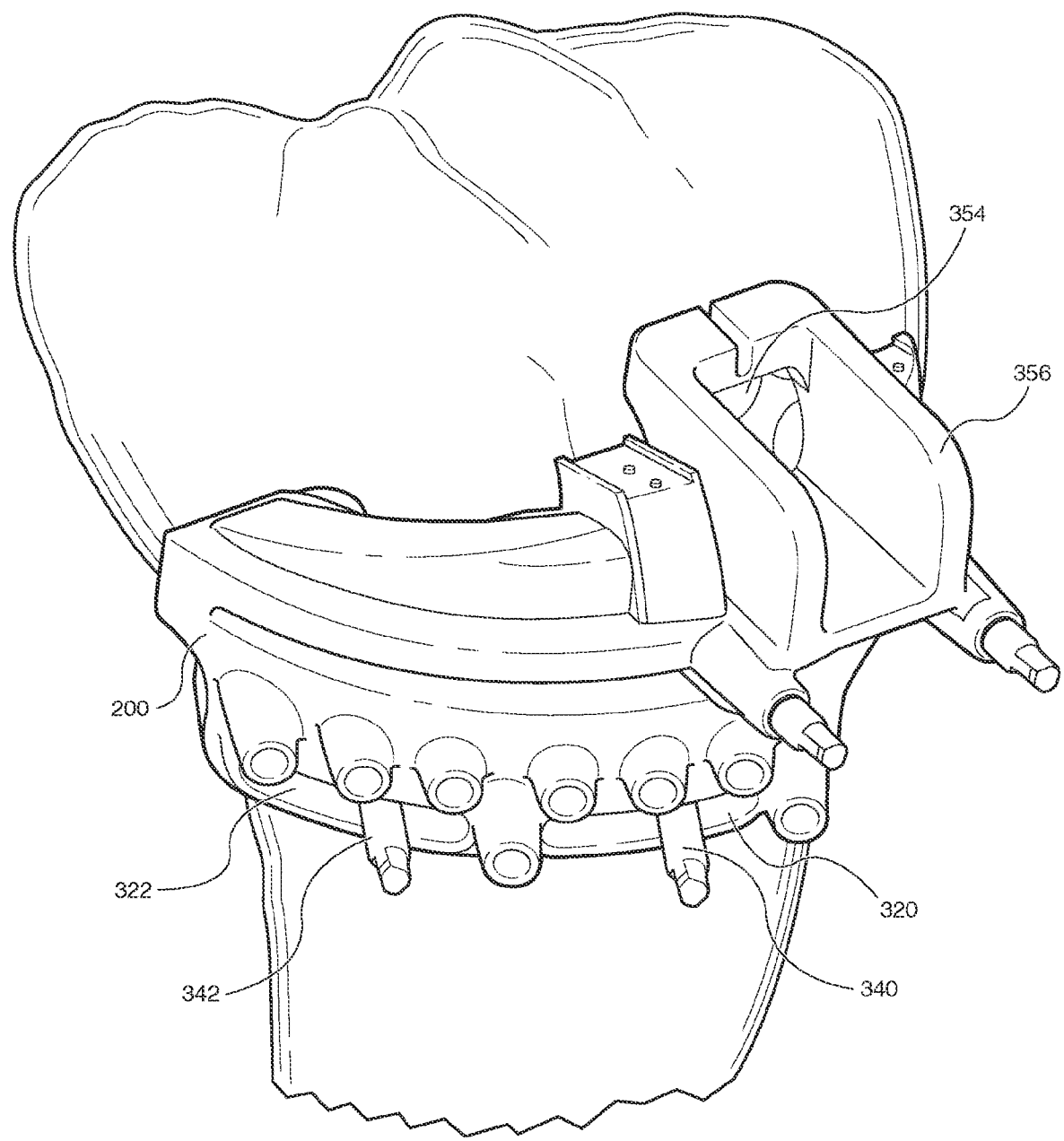

The operator then takes the knee to flexion (FIGS. 11 and 14) and removes the tibial cutting block 200 off the pins 340, 342. The operator can then place the knee in extension, (FIG. 12), and use protuberances 350 on bridge 16 to place a mark 352 on the tibia that indicates the neutral extension rotation of the femur relative to the tibia, i.e., the native alignment of the femur and tibia. After placing the knee back in flexion, the operator shifts up and replaces the cutting block 200 on the pins 340, 342 through the slots 320, 322 (FIGS. 15A and 15B). The operator can view the mark 352 through a window 354 defined in the alignment member 356 of the cutting block 200. By centering the mark 352 in the window 354, the operator positions the cutting block 200 in line with the native alignment of the femur and tibia.

Referring to FIG. 16, still in flexion, the surgeon moves the cutting block 200 on the pins 340, 342 to adjust and determine the medial-lateral and internal-external positions which best fit the cruciate ligaments 360, anterior tibia geometry and posterior femur intercondylar notch. The operator can use eminence cutting slots 240, 242 to visualize the location of the eminence resections, and a slot 358 in the alignment member 356 to visualize the alignment of the cutting block 200 with a posterior landmark.

Figure 17:
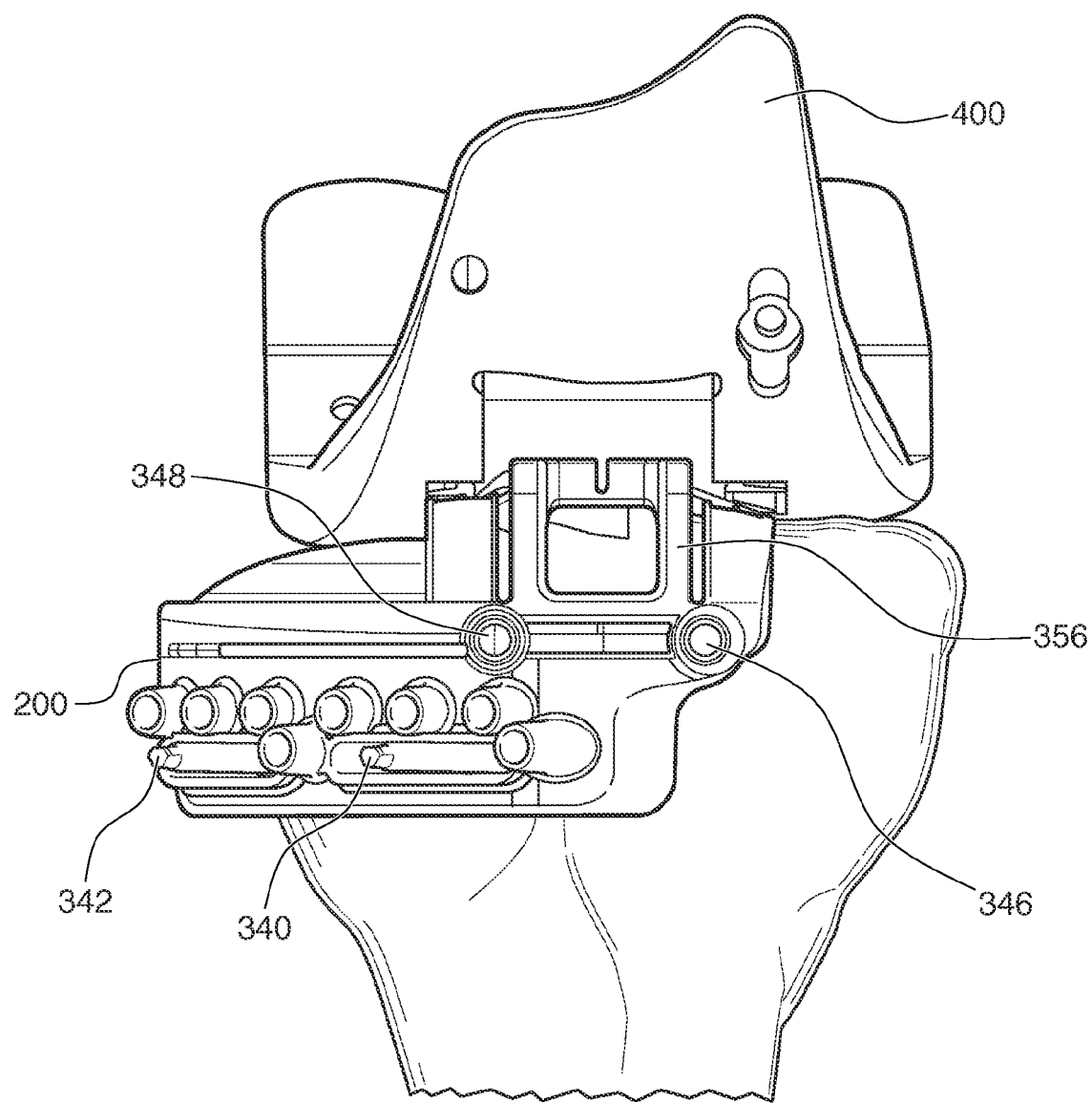
FIG. 17 illustrates the gauge assembly of FIG. 13 and a femur trial with the patient's leg in extension.
Figure 18:
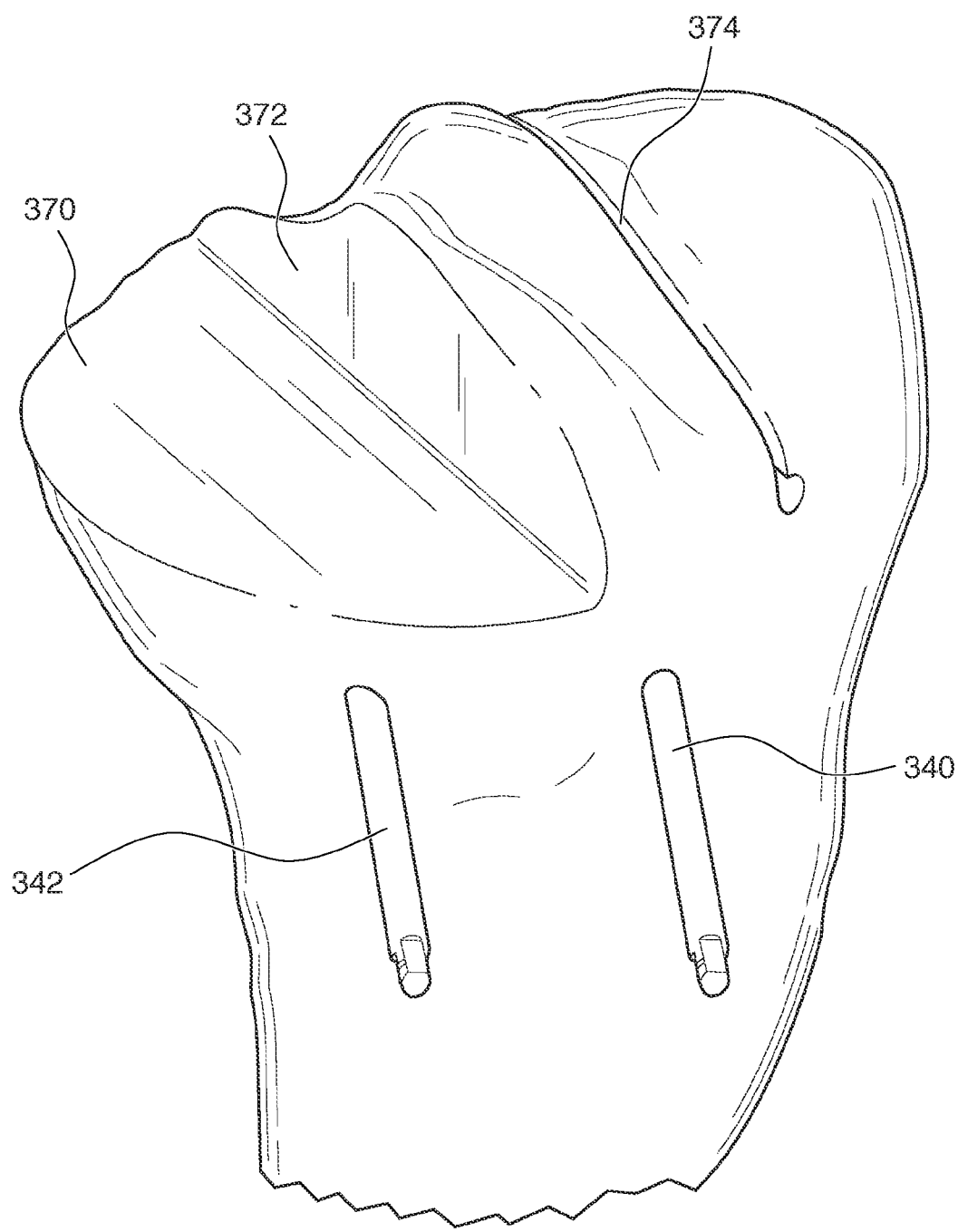
FIG. 18 illustrates tibia resections.

Referring to FIG. 17, with the cutting block 200 in the optimal position and a femur trial 400 placed on the distal femur, the operator takes the knee to extension to ensure there is adequate compatibility of the cutting block 300 relative to the anterior femur intercondylar notch. The operator then pins through eminence defining pin guides 346, 348 of the cutting block 200 and completes the medial plateau, medial eminence and lateral eminence resections 370, 372, 374 (FIG. 18). If after medial balancing the resection needs to be altered, the operator can use an alternative pin guide set and reposition the block 200 to mate with the medial-lateral and internal-external positions of the existing eminence resections.

IV. Avoid the Interactions Between and Error Propagations Amongst the Several Degrees of Freedom Due the Design of Conventional Patient-Matched Instrumentation The aforementioned devices, features and methods do not set all degrees of freedom simultaneously. When all degrees of freedom are set simultaneously, each degree of freedom (i.e. superior-inferior, varus-valgus, flexion-extension, internal-external, medial-lateral) becomes a function of the patient's particular anatomy and the value of each of the other degrees of freedom. The effect is that if a deviation is made by the operator in any one of the degrees of freedom from the pre-operative plan as indicated by the conforming surfaces of the cutting guide, all other degrees of freedom are affected to varying degrees depending on the patient's particular anatomy. By separating the degrees of freedom from one another and fixing each in a stepwise fashion, the cross-talk between degrees of freedom can be minimized or eliminated.

Other embodiments are within the scope of the following claims. For example, rather than the paddles being frangibly connected to the cutting block, the cutting block can be used as a drill guide to drill two holes into the tibia while the patient's leg is in extension. The guide assembly can then be removed, the patient's leg placed into flexion, the guide assembly slid back into place on the pins, and the tibial resection performed.

Figure 19:
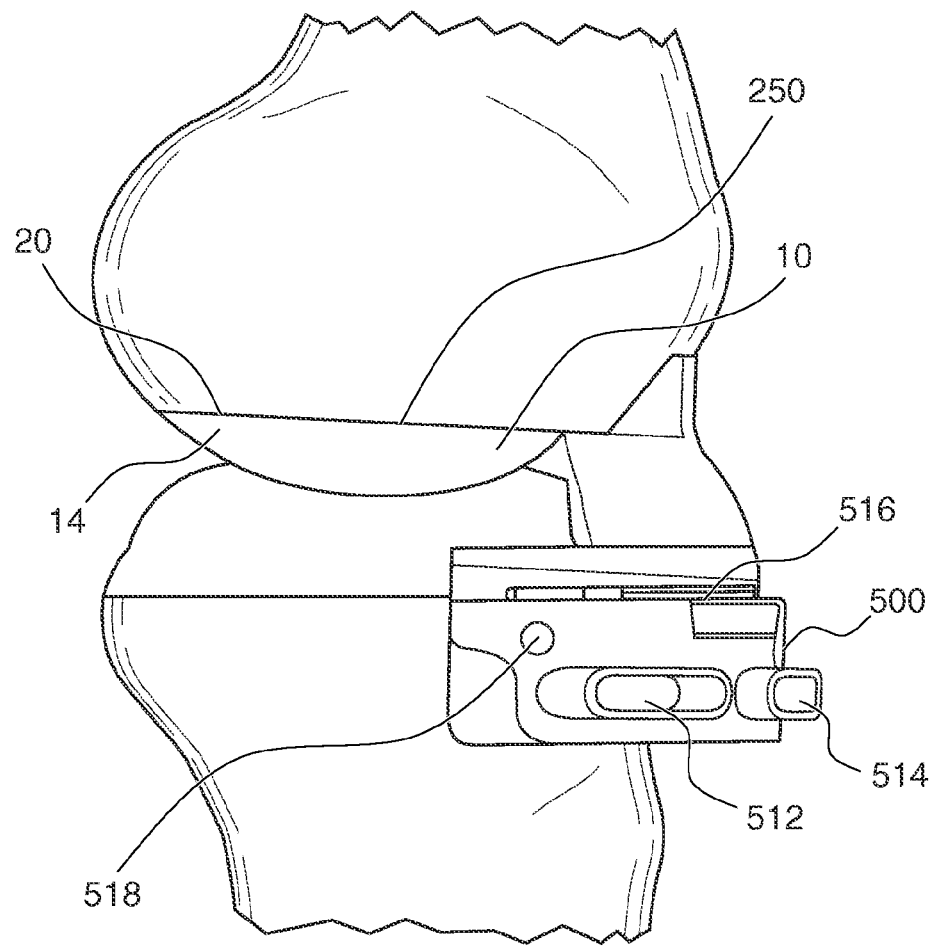
FIG. 19 is a view of another embodiment of a gauge assembly including a distal femur gauge and a tibial cutting block positioned between the femur and tibia.
Figure 20:
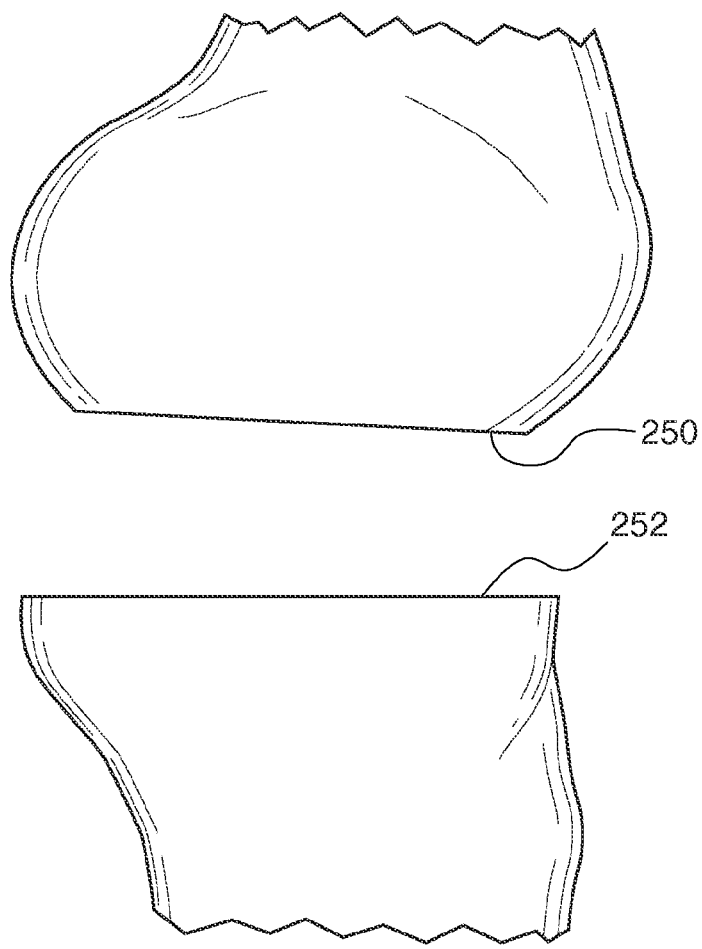
FIG. 20 is a side view of a resected femur and tibia.
Figure 21:
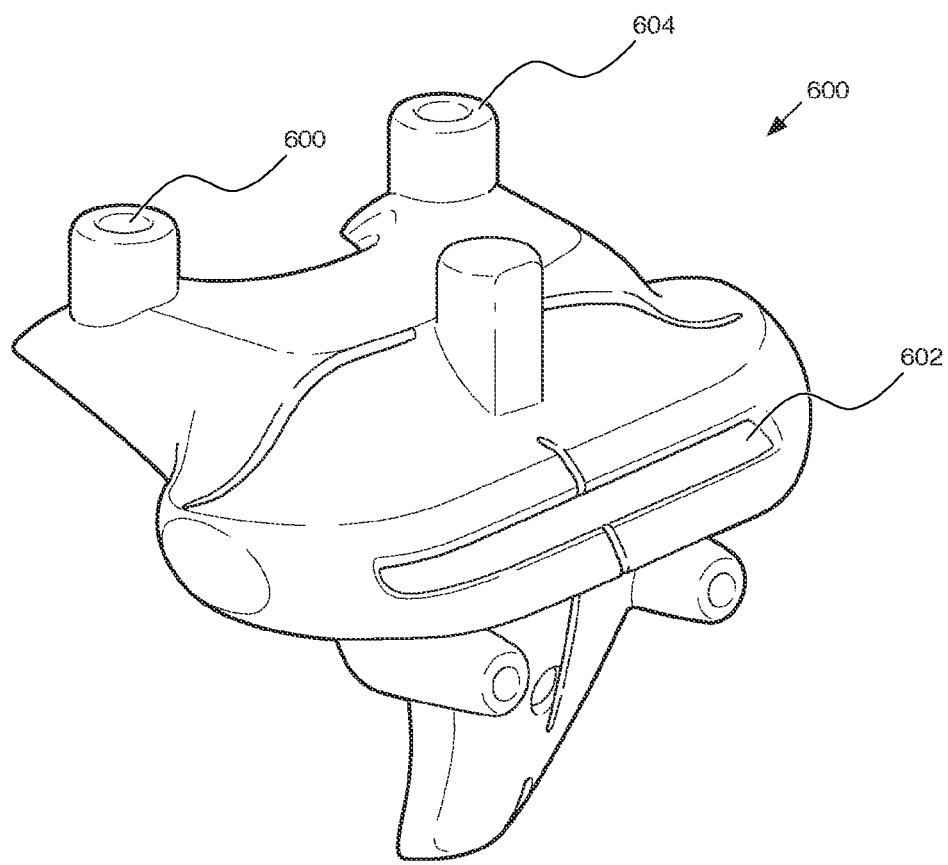
FIG. 21 is a perspective view of a prior art distal femur cutting block.
Figure 22:
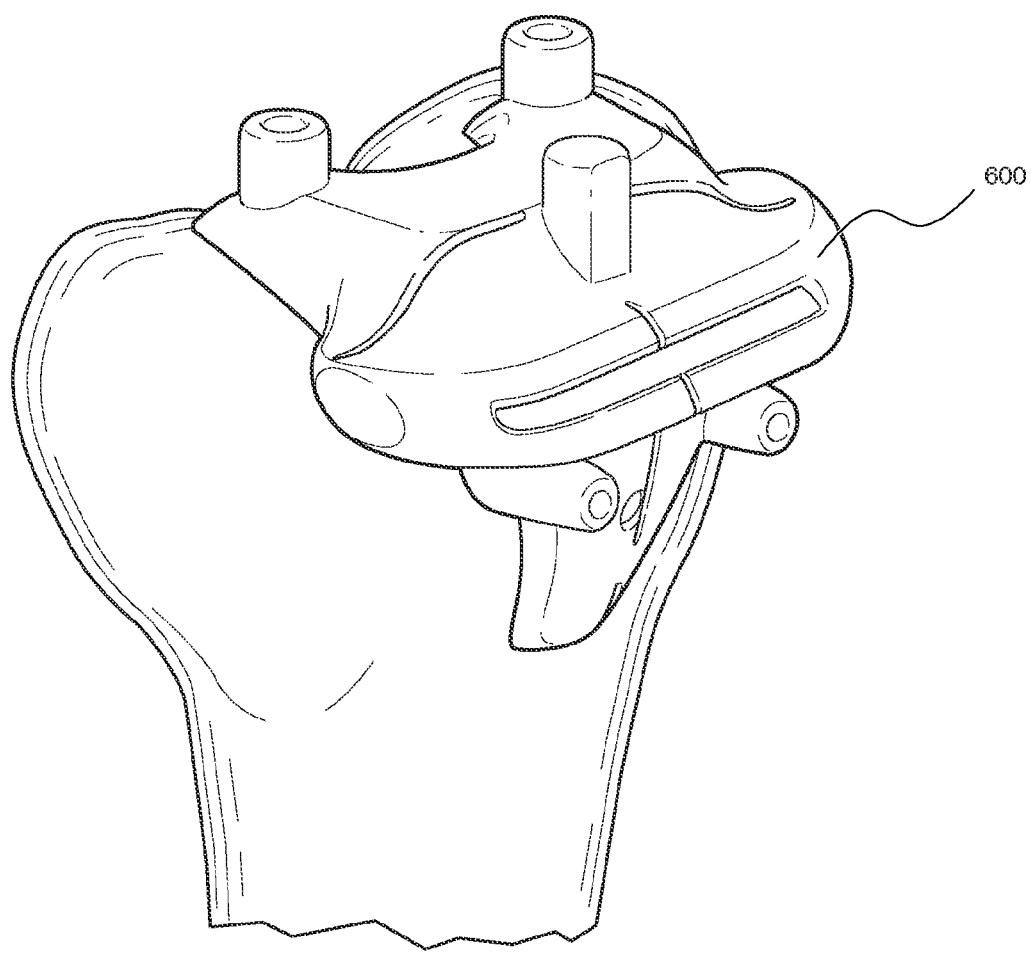
FIG. 22 illustrates the distal femur cutting block of FIG. 21 positioned on a femur.

Referring to FIGS. 19 and 20, a patient-matched tibial cutting block 500 of a guide assembly 510 including a distal femur gauge 10 includes slots 512, 514 that permit the guide assembly 510 to be adjusted in the medial-lateral and internal-external rotation degrees of freedom when pins extending into the tibia are received in the slots 512, 514. Cutting block 500 defines a slot 516 for guiding a saw blade to make medial and/or lateral plateau resections on the proximal tibia. As illustrated in FIG. 19, with the gauge 10 placed against the femur resection 250, and the patient's leg held in extension, slot 516 is positioned relative to the tibia to form the plateau resections 252. The slot 516 is spaced from the proximal-facing paddle surfaces 18, 20 a distance equal to the space required by the implants. In use, after making the distal femur resection and assessing the resection using the distal femur gauge 10, with the leg in extension, pins are placed into the tibia through the slots 512, 514 and the position of the guide assembly 510 is adjusted. When the operator is satisfied with the position of the cutting block 500, the cutting block is pinned in place using hole 518 and the tibial resection is made using slot 516.

Figure 23:
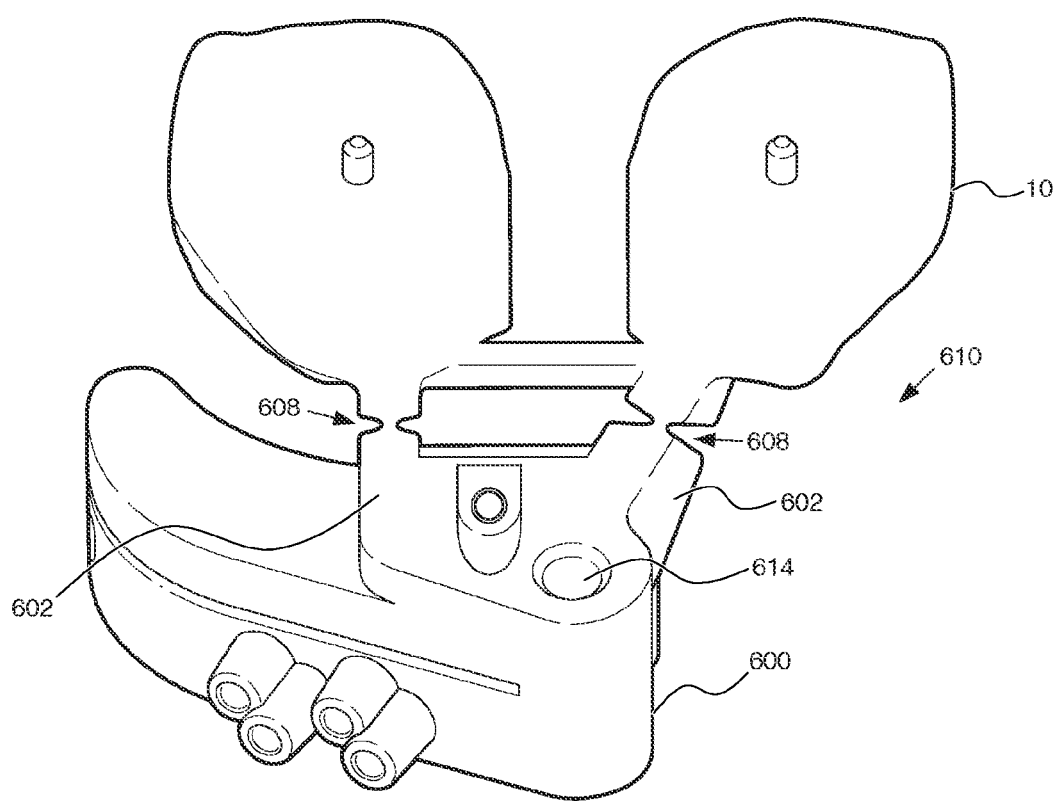
FIG. 23 is a perspective top view of another embodiment of a gauge assembly including a distal femur gauge and a tibial cutting block.
Figure 24A:
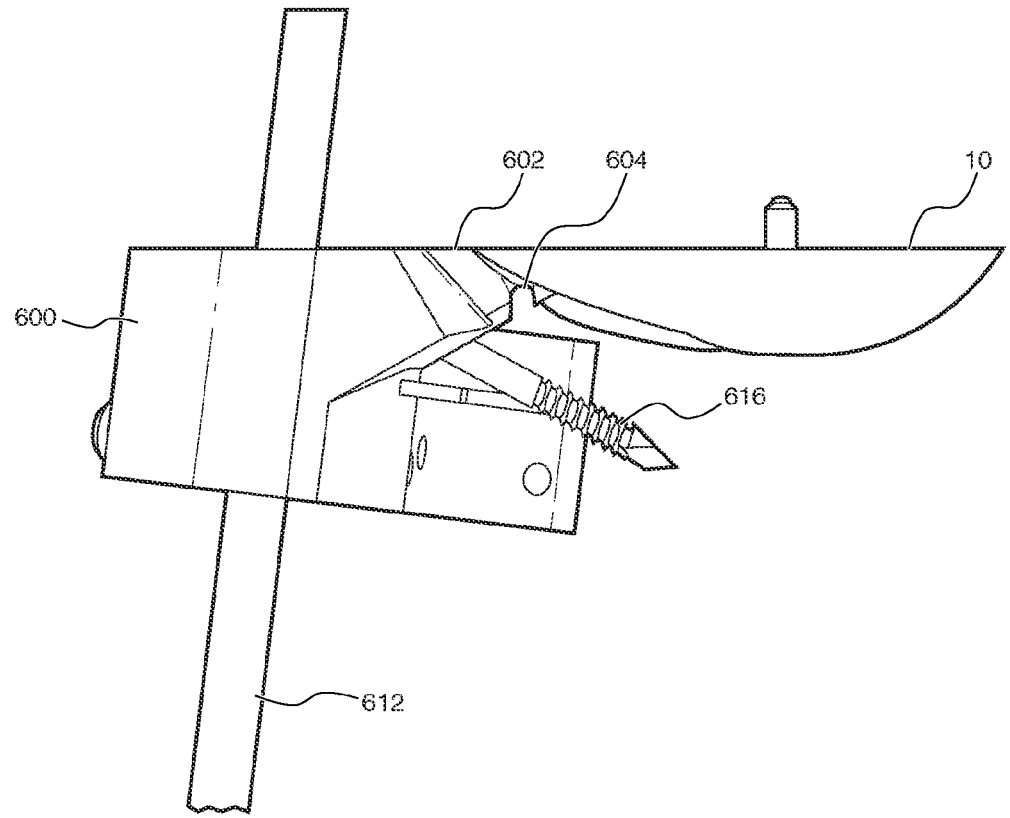
FIG. 24A is a side view of the gauge assembly of FIG. 23.
Figure 24B:
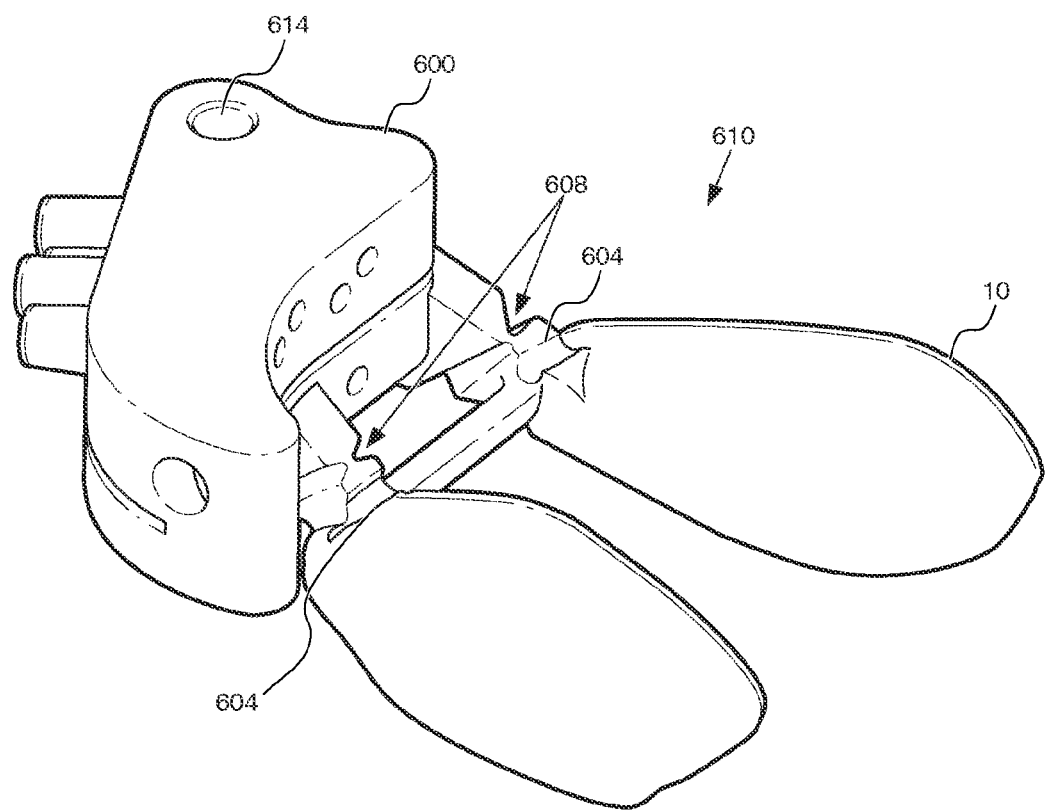
FIG. 24B is a perspective bottom view of the gauge assembly of FIG. 23.

The pin guide holes 324, 325, 326, 328, 329, 330 permit discreet adjustment of the posterior slope of the proximal tibial resection plane. Referring to FIGS. 23, 24A and 24B, according to another embodiment, a patient-matched tibial cutting block 600 of a guide assembly 610 including a distal femur gauge 10, for use in, for example, forming a complete proximal tibial resection, permits fine adjustment of the posterior slope of the proximal tibial resection plane. The guide assembly 610 includes flexible elements, for example, semi-flexible arms 602, that connect the tibial cutting block 600 and the distal femur gauge 10. The flexible arms 602 allow the tibial cutting block 600 to pivot relative to the distal femur gauge 10 and the tibia bone to permit fine adjustment of the posterior slope of the proximal tibial resection plane prior to pinning the tibial cutting block in place.

The flexible arms 602 each define a groove 604 that forms a pivot region about which the arms 602 flex. Each arm 602 also has a notched region 608 that permits the operator to separate the tibial cutting block 600 and the distal femur gauge 10 after the tibial cutting block 600 is pinned in place by severing the aims 602 at the notched regions 608, as discussed below.

Figure 25:
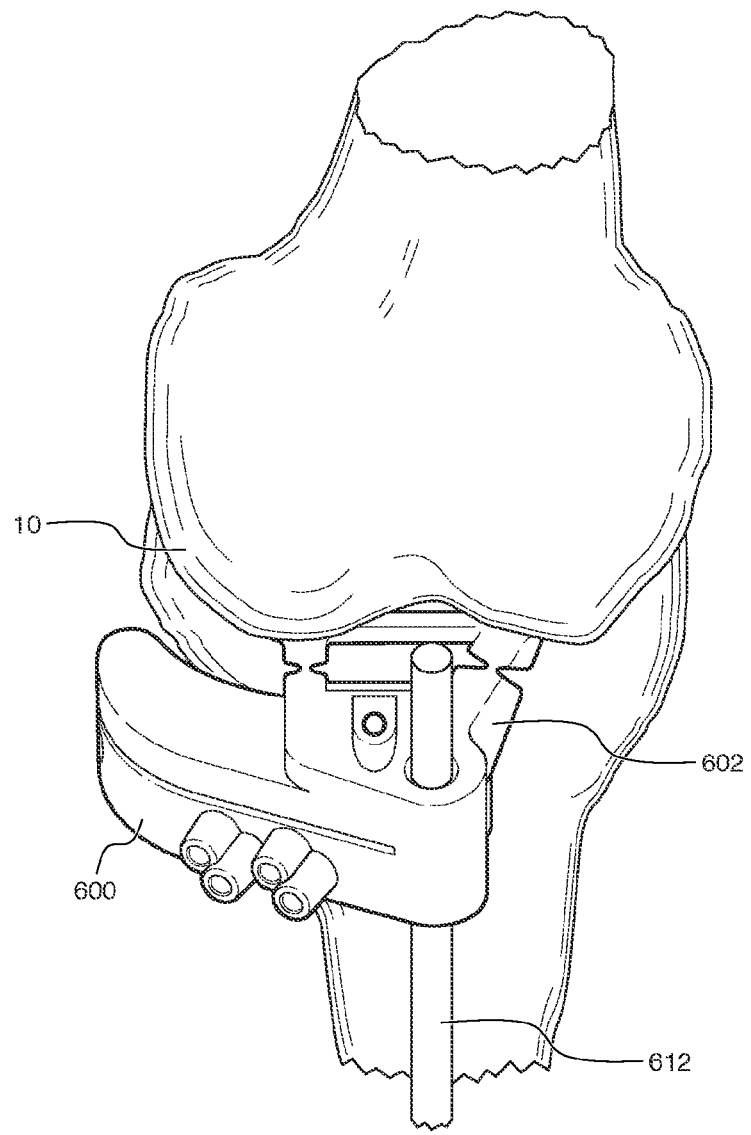
FIG. 25 is a view of the gauge assembly of FIG. 23 positioned between a femur and tibia.
Figure 26:
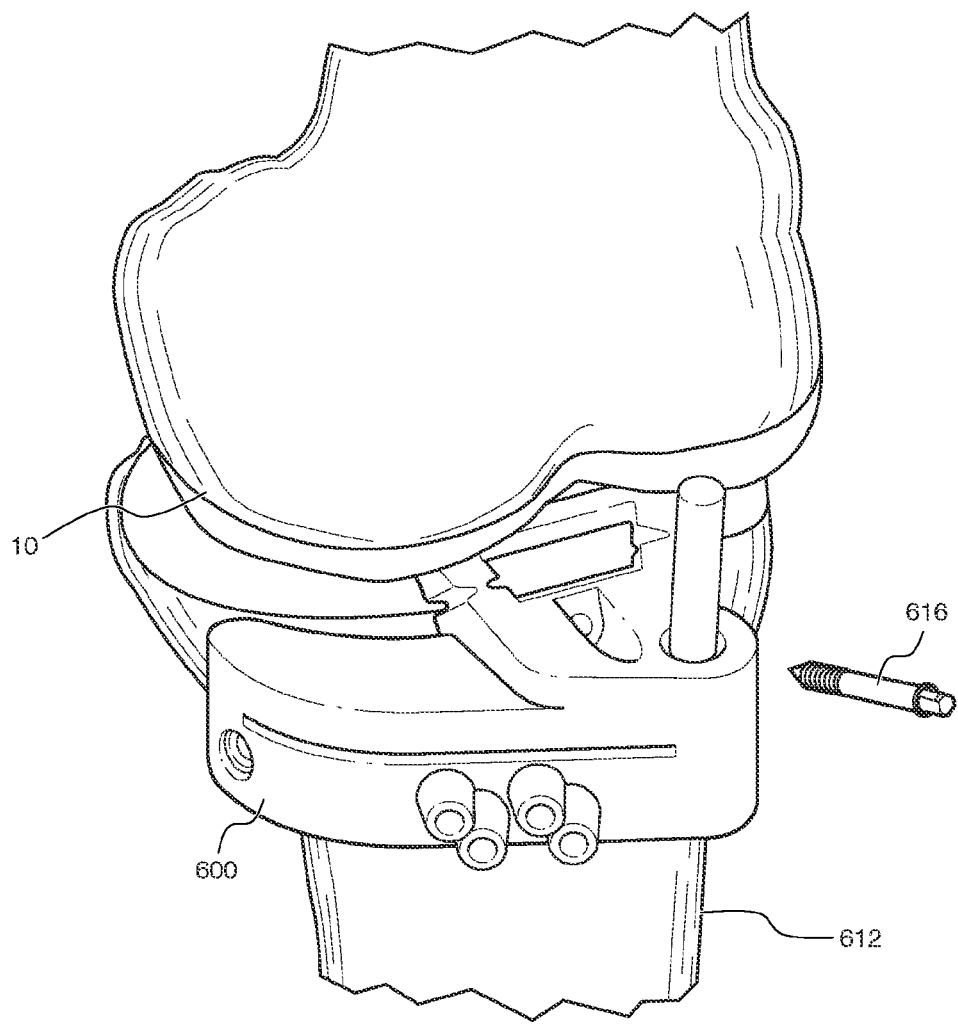
FIGS. 26-28 illustrate additional steps in the use of the gauge assembly of FIG. 23.
Figure 27:
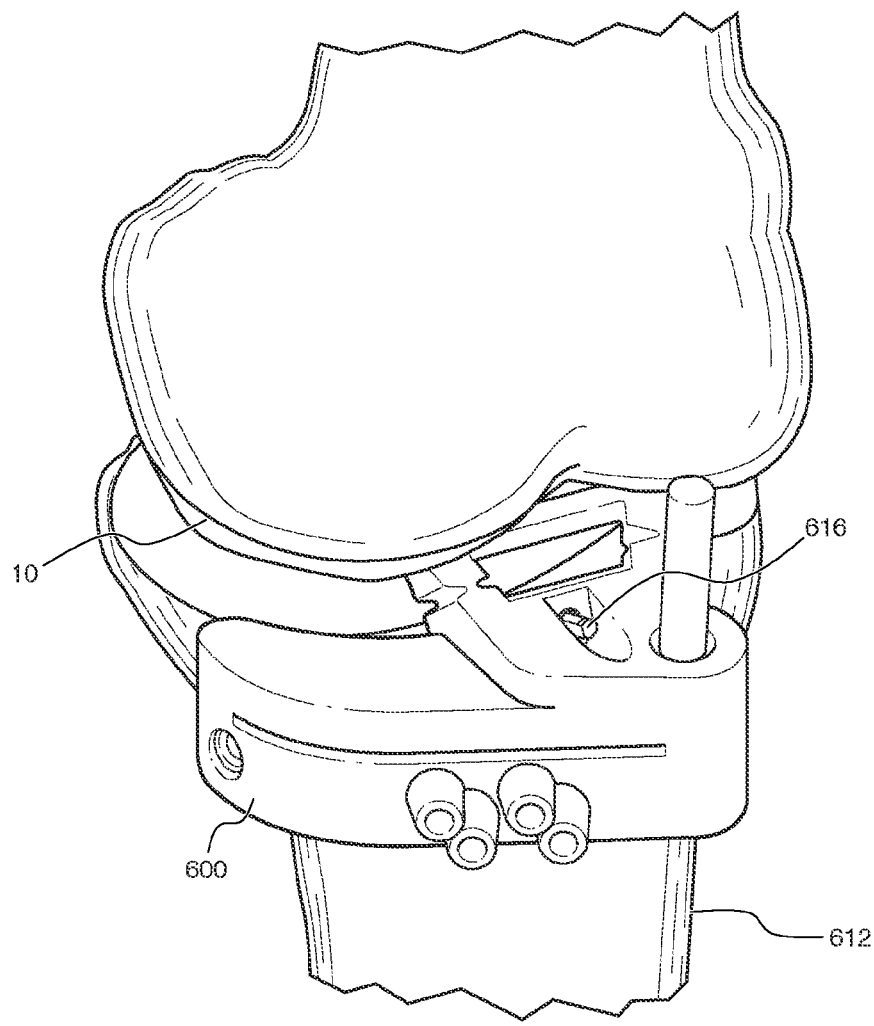

Referring also to FIG. 25, the guide assembly 610 is used with a drop down rod 612 received in a through hole 614 in tibial cutting block 600. The operator uses the drop down rod 612 to determine when the desired posterior slope has been achieved. The operator can adjust the posterior slope by pivoting the tibial cutting block 600 by hand, i.e., by torqueing the drop down rod 612, or, alternatively, an adjustment mechanism, for example, a threaded pin 616 (FIGS. 24A and 26), can be used. The pin 616 is received through an angled hole 618 in the tibial cutting block 600. When the operator advances the pin 616 into the tibia and tightens the pin (FIG. 27), the tibial cutting block 600 is pulled toward the tibia while pivoting about the pivot regions 604 of the aims 602. The amount the tibial cutting block 600 pivots is determined by how much the operator tightens the pin 616. The pivoting of the tibial cutting block 600 acts to decrease the posterior slope of the resection plane.

Figure 28:
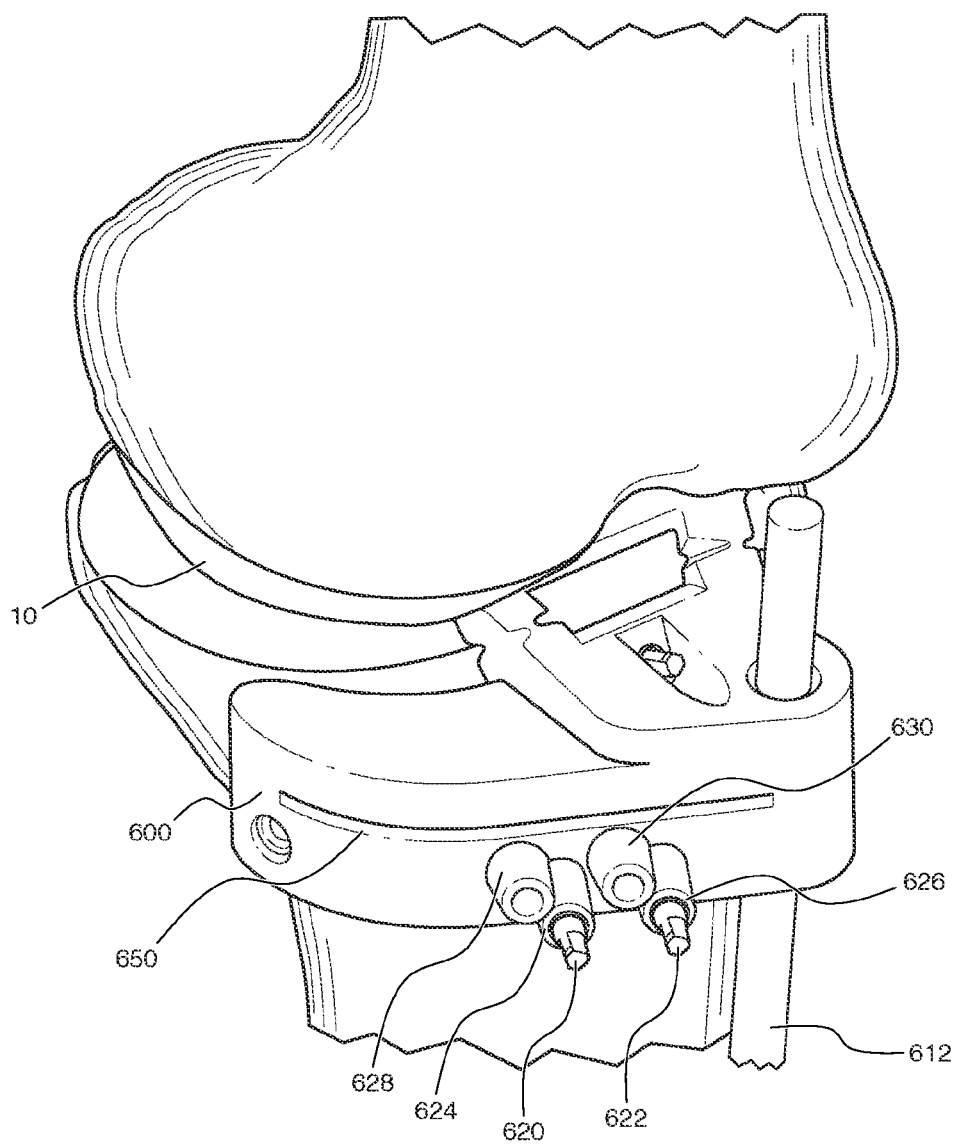
Figure 29:
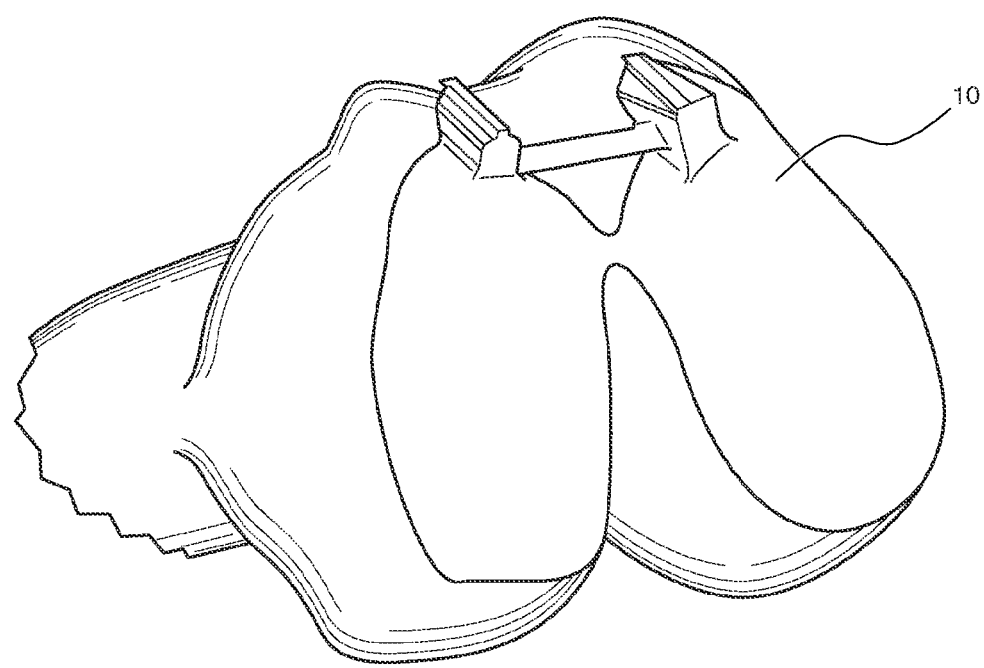
FIGS. 29-31 show the distal femur gauge and a tibial cutting block after separation.
Figure 30:
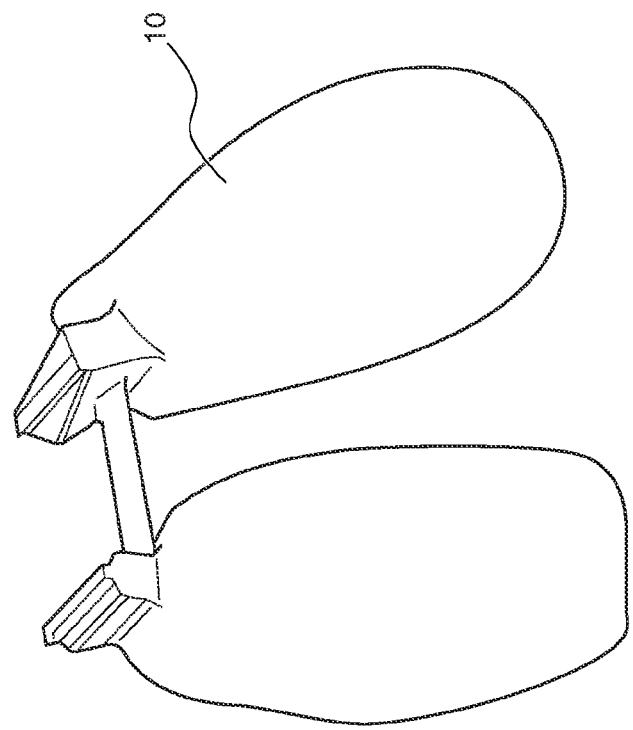
Figure 31:
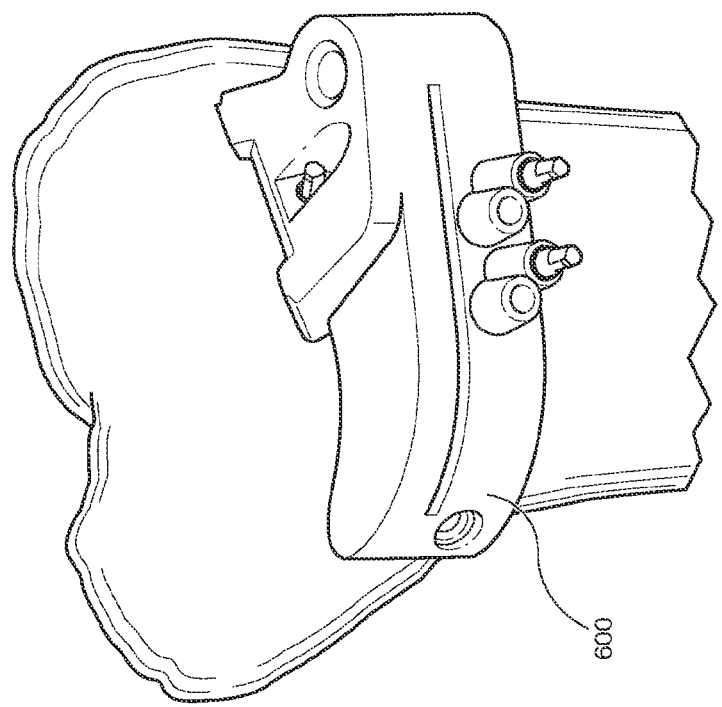

Referring to FIG. 28, when the desired posterior slope is obtained, as indicated by the drop down rod 612, two parallel pins 620, 622 are placed in pin holes 624, 626 to fix the position of the tibial cutting block 600. Referring to FIGS. 29-31, after the position of the tibial cutting block 600 is fixed, the tibial cutting block 600 and distal femur gauge 10 are separated by cutting arms 602 at notched regions 608. The tibia plateau resection is made using resection slot 650.

Placement of the pins 620, 622 in pin holes 624, 626 in FIG. 28, and the subsequent use of the same pin holes 624, 626 during tibial resection accommodates situations where the operator determines there is too much posterior slope and tightens the pin 616 to decrease the slope. To accommodate situations where the operator determines there is too little slope, a second set of pin holes 628, 630 are provided that have a larger posterior slope angle by about 3 to 6 degrees, for example, by about 3 degrees, than pin holes 624, 626. For example, with a 3 degree variance in slope angle between the sets of pin holes, if the operator determines there is too little slope by 2 degrees, the operator can tighten the pin 616 to decrease the slope by an additional 1 degree. Two parallel pins 620, 622 are then placed in pin holes 628, 630 and the tibial cutting block 600 and distal femur gauge 10 are separated by cutting arms 606 at notched regions 608. The operator then slides the tibial cutting block 600 off the pins 620, 622, and places the tibial cutting block 600 back onto the pins 620, 622 through holes 624, 626, thus providing the desired alignment.

Figure 32:
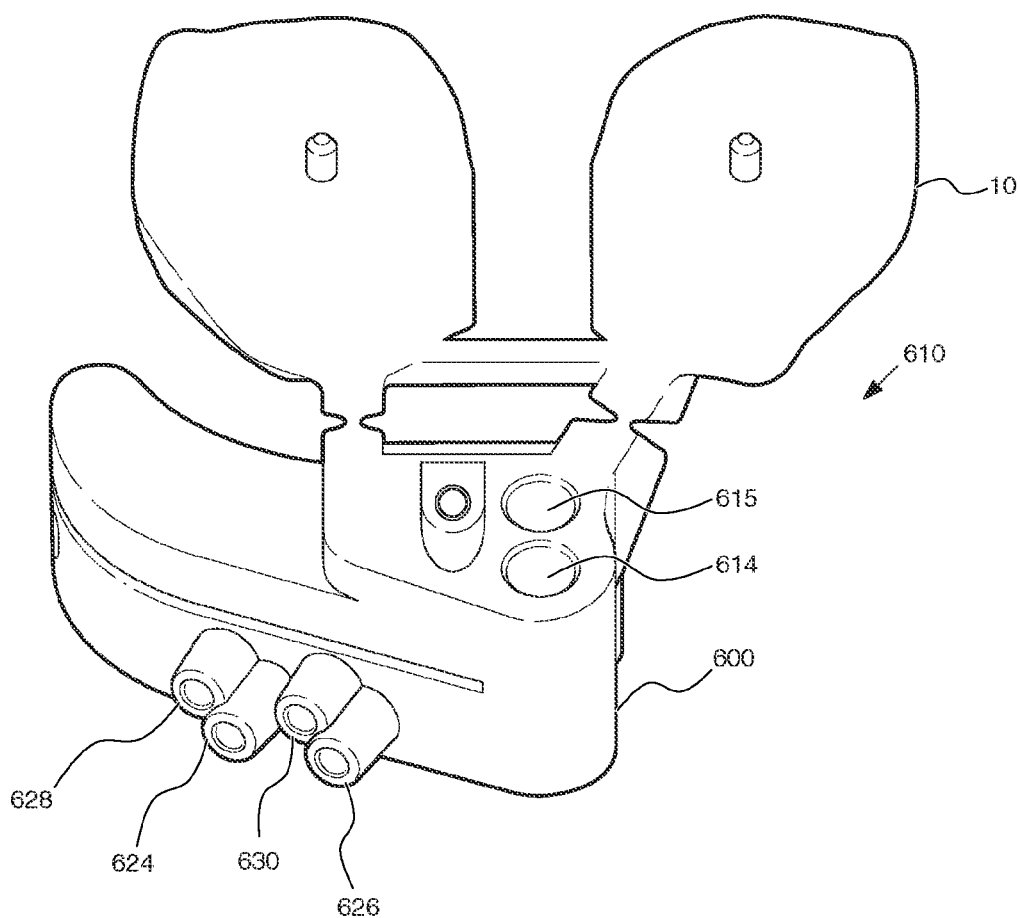
FIG. 32 is a perspective view of the gauge assembly of FIG. 23 including a second drop down rod hole.

Referring to FIG. 32, to facilitate visualizing the various alignment options, the patient-matched tibial cutting block 600 can include more than one alignment rod connecting features, for example, holes 614 and 615, which correspond to the alignments which are associated to each of the sets of pin holes 628, 630 and 624, 626. For example, in situations where there is too little slope, rather than estimating when the drop down angle reaches 3 degrees, the second hole 615 is provided in the tibial cutting block 600 offset by 3 degrees relative to the hole 614. Thus, if with the drop down rod 612 located in hole 614, the operator determines there is too little slope, the operator can move the drop down rod to hole 615 and tighten the pin 616 until the drop down rod is at zero degrees.

In another embodiment, the ability to adjust the proximal tibial resection before and after the resection is made is provided by configuring one side of a patient-matched proximal tibia cutting block to conform to the anterior tibia and extensions of the cutting block contact proximal medial and/or proximal lateral tibial condyles. A set of primary pin holes are positioned for fixation to the anterior tibia and are perpendicular to the normal of the resection plane. The cutting block includes sets of alternative pin holes designed to change one or more degrees of freedom, for example: resection amount, varus/valgus, flexion/extension. The operator mates the patient-matched block to the tibia and pins through the primary holes. Then, if the operator decides before or after the tibia resection is made to deviate from the pre-operative plan or correct for an error, the user can disconnect the extensions via a breaking or cutting feature, pull off the patient-matched block, and replace the block on the primary pins by sliding the pins through an alternative set of holes.

The operator preferably also has the ability to adjust intra-operatively the distal femur resection after the distal femur resection is made. As with the ability to adjust the proximal tibial resection, a patient-matched distal femoral cutting block can likewise have one side configured to conform to the anterior femur and extensions of the cutting block that contact distal medial and/or distal lateral condyles. A set of primary pin holes are positioned for fixation to the anterior femur and are perpendicular to the normal of the resection plane. The distal femoral cutting block includes sets of alternative pin holes designed to change one or more DOF, for example: resection amount, varus/valgus, flexion/extension. After pinning the cutting black through the primary pin holes, the user can disconnect the extensions via a breaking or cutting feature, pull off the cutting block, and replace the block on the primary pins by sliding the pins through an alternative set of holes.

Prior to any resections being made, with the tibia and femoral cutting blocks attached, the operator can assess the relationship between the blocks (and therefore the resections, and therefore the implants). The operator can then adjust one or both of the blocks using an alternative set of holes such that the relationship of the blocks to each other and to the limb as a whole is desirable or meets some criteria which could be physically assessed with a third device such as a gauge or set of gauges which reference each of the two blocks to make a comparison.

In an alternative embodiment of a distal femoral cutting block providing the ability to adjust intra-operatively the distal femur resection after the distal femur resection is made, the cutting block has two or more sides that enable the cutting block to be reversed, flipped, rotated or alternatively placed and caused to mate to the femur with an alternative set of contacting features which guide the resection plane in an alternative orientation relative to the anatomy.

The operator preferably also has the ability to adjust intra-operatively the slope of the tibial implant after the tibia resection is made. The tibial slope can be altered for balance by adjusting the implant after all resections are made if additional slope can be built into the implant safely. The operator can determine the desired slope using alternative insert trials representing alternatively sloped implants. If the operator chooses to recut the tibia at a different slope, alternatively sloped insert trials can be used as gauges for how the joint may feel after an intended resection.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A distal femur gauge, comprising:
   a medial condyle paddle;
   a lateral condyle paddle connected to the medial condyle paddle, each condyle paddle having a shape and size corresponding to a patient's resected femur based on a pre-operatively planned distal resection of the patient's femur; and
   a bridge that adjoins the medial condyle paddle and the lateral condyle paddle, the bridge including at least one protuberance;
   wherein the lateral and medial condyle paddles each have a proximal facing surface that is flat and configured to conform to a distal end of the patient's femur after the distal resection of the patient's femur; and
   wherein the lateral and medial condyle paddles each further comprise a distal facing surface, the distal facing surface of the lateral condyle paddle being contoured to replicate the patient's native lateral condyle, the distal facing surface of the medial condyle paddle being contoured to replicate the patient's native medial condyle.

2. The distal femur gauge of claim 1 wherein the lateral and medial condyle paddles are each replicas of the resected femur based on preoperatively planned condyle resections.

3. The distal femur gauge of claim 1 wherein the lateral and medial condyle paddles are shaped and sized to aid in correcting a limb mal-alignment.

4. The distal femur gauge of claim 1 wherein the lateral and medial condyle paddles include features that permit intra-operative anterior-posterior and/or internal-external adjustment of the position of the distal femur gauge.

5. The distal femur gauge of claim 1, further comprising a pin positioned on, and outwardly extending from, the distal facing surface of each of the lateral condyle paddle and the medial condyle paddle, and wherein the pin is located at a position at which the pin can be inserted into a prepared hole in the distal end of the patient's femur after the distal resection of the patient's femur.

6. The distal femur gauge of claim 5, wherein each of the lateral condyle paddle and the medial condyle paddle includes at least one pin hole that extends through both the proximal facing surface and the distal facing surface.

7. The distal femur gauge of claim 6, wherein the at least one pin hole of the medial condyle paddle includes at least an elongated slot.

8. The distal femur gauge of claim 6, wherein the at least one pin hole of each of the lateral condyle paddle and the medial condyle paddle comprises a first pin hole and a second pin hole, wherein the first pin hole is positioned to facilitate adjustment of an anterior-posterior positon of the distal femur guide, and wherein the second pin hole is positioned to facilitate adjustment of an internal-external rotation of the distal femur guide.

9. The distal femur gauge of claim 6, wherein the at least one protuberance is positioned on the bridge at a location that corresponds to a location of a neutral extension rotation of the patient's femur relative to the patient's tibia.

10. The distal femur gauge of claim 6, wherein the at least one protuberance is shaped and positioned to provide a hyperextension stop.

11. The distal femur gauge of claim 10, wherein the at least one protuberance is removable from the bridge.

* * * * *